(12) United States Patent
Silbert et al.

(10) Patent No.: US 9,335,336 B2
(45) Date of Patent: May 10, 2016

(54) AUTOMATED SAMPLE HANDLING INSTRUMENTATION, SYSTEMS, PROCESSES, AND METHODS

(75) Inventors: Rolf Silbert, Del Mar, CA (US); David Opalsky, San Diego, CA (US); David Aaron Buse, San Diego, CA (US); Robert J. Rosati, Carlsbad, CA (US); Olev Tammer, New York, NY (US)

(73) Assignee: GEN-PROBE INCORPORATED, San Diego, CA (US)

( * ) Notice: Subject to any disclaimer, the term of this patent is extended or adjusted under 35 U.S.C. 154(b) by 0 days.

(21) Appl. No.: 13/608,876

(22) Filed: Sep. 10, 2012

(65) Prior Publication Data

US 2013/0065797 A1 Mar. 14, 2013

Related U.S. Application Data

(60) Provisional application No. 61/532,765, filed on Sep. 9, 2011.

(51) Int. Cl.
| | |
|---|---|
| *G01N 35/00* | (2006.01) |
| *G01N 35/10* | (2006.01) |
| *G01F 23/26* | (2006.01) |
| *G01N 1/28* | (2006.01) |

(Continued)

(52) U.S. Cl.
CPC .......... *G01N 35/0099* (2013.01); *G01F 23/265* (2013.01); *G01N 35/1016* (2013.01); *G01N 35/1079* (2013.01); *C40B 60/12* (2013.01); *G01N 2035/00524* (2013.01); *G01N 2035/00752* (2013.01); *G01N 2035/00811* (2013.01); *G01N 2035/0405* (2013.01); *G01N 2035/1062* (2013.01)

(58) Field of Classification Search
CPC .............. G01N 2035/1046; G01N 2035/1062; G01N 2035/0405; G01N 2035/1018
See application file for complete search history.

(56) References Cited

U.S. PATENT DOCUMENTS

| | | | |
|---|---|---|---|
| 4,478,095 A | 10/1984 | Bradley et al. | |
| 4,609,017 A | 9/1986 | Coulter et al. | |

(Continued)

FOREIGN PATENT DOCUMENTS

| | | |
|---|---|---|
| CN | 101149367 A | 3/2008 |
| CN | 101218029 A | 7/2008 |

(Continued)

OTHER PUBLICATIONS

IP Australia Office Action, Australian Patent Application No. 2012305682, Mar. 7, 2014.

(Continued)

*Primary Examiner* — Neil N Turk
(74) *Attorney, Agent, or Firm* — Charles B. Cappellari; Richard Wydeven; David L. Devernoe

(57) ABSTRACT

The present invention provides a processing station for automatically processing a biological sample, a system for automated real-time inventory control of consumables within a biological sample handling or assay instrument, a high throughput random access automated instrument for processing biological samples, an automated instrument for processing or analysis of a sample, and processes for automated mucoid detection and elimination. Methods of using the disclosed instruments, mucoid detection processes, and systems to process and/or analyze samples are also disclosed.

32 Claims, 20 Drawing Sheets

(51) Int. Cl.
  *C40B 60/12* (2006.01)
  *G01N 35/04* (2006.01)

(56) References Cited

U.S. PATENT DOCUMENTS

| | | | |
|---|---|---|---|
| 4,794,085 A | | 12/1988 | Jessop et al. |
| 4,834,944 A | | 5/1989 | Wakatake |
| 4,977,786 A | | 12/1990 | Davis |
| 5,083,470 A | | 1/1992 | Davis |
| 5,260,872 A | * | 11/1993 | Copeland et al. ............... 435/13 |
| 5,314,825 A | | 5/1994 | Weyrauch et al. |
| 5,472,669 A | | 12/1995 | Miki et al. |
| 5,578,494 A | | 11/1996 | Clark et al. |
| 5,814,276 A | | 9/1998 | Riggs |
| 5,885,529 A | | 3/1999 | Babson |
| 5,885,530 A | | 3/1999 | Babson |
| 6,060,022 A | | 5/2000 | Pang |
| 6,141,602 A | | 10/2000 | Igarashi et al. |
| 6,202,278 B1 | * | 3/2001 | Nakayama et al. ......... 29/426.3 |
| 6,257,091 B1 | | 7/2001 | Cohen et al. |
| 6,290,907 B1 | | 9/2001 | Takahashi et al. |
| 6,353,774 B1 | | 3/2002 | Goldenberg |
| 6,409,968 B1 | | 6/2002 | Takahashi |
| 6,572,824 B1 | | 6/2003 | Tenney et al. |
| 6,599,476 B1 | | 7/2003 | Watson |
| 6,669,910 B1 | | 12/2003 | Bienhaus et al. |
| 6,883,958 B2 | | 4/2005 | Mayer |
| 6,974,294 B2 | | 12/2005 | Pressman |
| 7,141,213 B1 | | 11/2006 | Pang |
| 7,233,838 B2 | | 6/2007 | Barry et al. |
| 7,264,432 B2 | | 9/2007 | Wiggli |
| 7,284,900 B2 | | 10/2007 | Mayer |
| 7,291,309 B2 | | 11/2007 | Watson |
| 7,316,779 B2 | | 1/2008 | Pressman |
| 7,377,027 B2 | | 5/2008 | Mayer |
| 7,390,458 B2 | | 6/2008 | Burow |
| 7,479,391 B2 | | 1/2009 | Bjornson |
| 7,501,094 B2 | | 3/2009 | Bysouth |
| 7,572,638 B2 | | 8/2009 | Pressman |
| 7,628,954 B2 | | 12/2009 | Gomm et al. |
| 7,771,662 B2 | | 8/2010 | Pressman |
| 7,807,476 B2 | | 10/2010 | Pressman |
| 7,846,384 B2 | | 12/2010 | Watson |
| 7,985,375 B2 | | 7/2011 | Edens |
| 8,008,066 B2 | | 8/2011 | Lair |
| 8,038,942 B2 | | 10/2011 | Ping et al. |
| 8,355,132 B2 | | 1/2013 | Xia |
| 8,357,538 B2 | | 1/2013 | Self |
| 2001/0034064 A1 | | 10/2001 | Turner |
| 2002/0090320 A1 | | 7/2002 | Burow |
| 2002/0150450 A1 | | 10/2002 | Bevirt |
| 2003/0059347 A1 | | 3/2003 | Ostgaard et al. |
| 2003/0099573 A1 | * | 5/2003 | Tseung et al. ................. 422/63 |
| 2003/0207456 A1 | | 11/2003 | Ostgaard et al. |
| 2004/0265173 A1 | * | 12/2004 | Matsumoto et al. ............ 422/64 |
| 2004/0265855 A1 | | 12/2004 | Pessara |
| 2005/0058574 A1 | | 3/2005 | Bysouth |
| 2006/0210432 A1 | * | 9/2006 | Victor ............................. 422/63 |
| 2006/0263248 A1 | * | 11/2006 | Gomm et al. ................... 422/63 |
| 2007/0059209 A1 | | 3/2007 | Pang |
| 2007/0123999 A1 | | 5/2007 | Raghibizadeh |
| 2007/0177778 A1 | * | 8/2007 | Massaro ............ G01N 35/1016 382/128 |
| 2007/0254277 A1 | | 11/2007 | Scrabeck et al. |
| 2008/0247914 A1 | * | 10/2008 | Edens et al. ................. 422/100 |
| 2009/0047179 A1 | | 2/2009 | Ping |
| 2009/0136386 A1 | | 5/2009 | Duffy |
| 2010/0126286 A1 | | 5/2010 | Self |
| 2010/0132484 A1 | | 6/2010 | Schacher |
| 2010/0288056 A1 | | 11/2010 | Clark |
| 2010/0288061 A1 | | 11/2010 | Hagen |
| 2011/0039709 A1 | | 2/2011 | Lips et al. |

FOREIGN PATENT DOCUMENTS

| | | |
|---|---|---|
| CN | 101784345 A | 7/2010 |
| EP | 0973039 A2 | 1/2000 |
| EP | 1 243 929 A1 | 9/2002 |
| EP | 1 589 344 A1 | 10/2005 |
| EP | 0918221 B1 | 9/2006 |
| EP | 2275810 A1 | 1/2011 |
| WO | 9116675 A1 | 10/1991 |
| WO | 9601994 A1 | 1/1996 |
| WO | 0138882 A1 | 5/2001 |
| WO | 0231747 A1 | 4/2002 |
| WO | 2005024385 A2 | 3/2005 |
| WO | 2006054964 A1 | 5/2006 |
| WO | 2006081612 A1 | 8/2006 |
| WO | 2008123882 A | 10/2008 |
| WO | 2008133708 A1 | 11/2008 |
| WO | 2009017511 A1 | 2/2009 |
| WO | 2009068555 A1 | 6/2009 |
| WO | 2010038852 A1 | 4/2010 |
| WO | 2010/056903 A1 | 5/2010 |
| WO | 2010056890 A | 5/2010 |
| WO | 2010056903 A | 5/2010 |
| WO | 2010057861 A2 | 5/2010 |

OTHER PUBLICATIONS

EPO, Communication pursuant to Rule 164(1) EPC, European Application No. 12829673.8, Mar. 25, 2015.
EPO, Communication pursuant to Rule 62 EPC, European Application No. 12829673.8, Jul. 7, 2015.
SIPO, Office Action, Chinese Patent Application No. 201280054253.6, Jun. 3, 2015.
SIPO, Supplementary Search Report, Chinese Patent Application No. 201280054253.6, Jun. 3, 2015.

* cited by examiner

AUTOMATED SAMPLE HANDLING INSTRUMENTATION, SYSTEMS, PROCESSES, AND METHODS

CROSS-REFERENCE TO RELATED APPLICATIONS

This application claims priority to U.S. patent application Ser. No. 61/532,765, filed Sep. 9, 2011, which is incorporated herein by reference.

FIELD OF THE INVENTION

The present invention relates to automated sample handling instrumentation, systems, processes, and methods.

BACKGROUND OF THE INVENTION

Clinical laboratory work often involves a number of repetitive tasks that are required to be performed quickly and with high precision. Given the desire to provide more rapid and accurate laboratory results, there has been a recent movement to automate laboratory procedures and assays. Though taking repetitive tasks out of the hands of laboratory technicians and having them performed by a machine may provide ergonomic and throughput benefits, the task of automating intricate biological procedures has been fraught with difficulties. One source of these difficulties is the fact that biological materials are often complicated materials to work with. Contamination, accuracy, and completeness of an assay or sample processing procedure are ever-present concerns when the instrument is doing the work of a skilled laboratory technician. Nevertheless, automated instruments hold the potential to reduce human error and offer a more consistent and repeatable series of sample manipulations and assays.

Accordingly there exists a need in the art to minimize laboratory technician handling time of biological specimens prior to assay, while ensuring that sample processing is completed accurately without the risk of contamination. The present invention addresses these and other needs.

None of the references described or referred to herein are admitted to be prior art to the claimed invention.

SUMMARY OF THE INVENTION

The present disclosure provides a processing station for automatically processing a biological sample, comprising: (a) a rotatable platform capable of mixing a biological sample, wherein the platform rotates around a central axis; (b) two or more container holders arranged on the X-Y plane in spatially distinct locations on the rotatable platform, wherein the container holders are adapted to hold different containers (wherein each of the different containers has a different size and/or shape) such that two or more different container holders are present; (c) a capping/decapping mechanism that is capable of capping/decapping the two or more different containers, wherein each of the two or more different containers have a different shape and/or a different shaped cap; (d) a data scanning mechanism capable of acquiring information about a container or its contents, wherein the data scanning mechanism is arranged such that the container can be scanned while positioned in one of the two or more container holders; and (e) a mucoid detection mechanism.

In one embodiment the processing station further comprises a drip tray arranged to be movably positioned under the one or more capping/decapping mechanisms. The drip tray is most frequently translatable in the X-Y plane. This translation often comprises rotation about a tertiary axis that is different than the central axis of the rotatable platform. Frequently, the drip tray extends outwardly from the tertiary axis and often the extension is effected by way of an arm, post, plate, panel, or blade extending outwardly from the tertiary axis. In other embodiments the drip tray is translatable in the X-, Y-, and/or Z-planes.

The mucoid detection of the processing station often comprises machine vision, reverse capacitive liquid level detection, or a combination thereof.

The processing station is also often positioned in a sample processing instrument comprising a sample input rack, a sample output rack, and incubator, a pipette tip tray, a reagent container, a waste bin for containing used consumables such as pipette tips and/or liquid waste.

The processing station frequently comprises an instrument inventory management system. Often the instrument inventory management system monitors the inventory of sample containers and reaction vessels in the input racks, the incubator(s), and/or the output racks. The instrument inventory management system also often further monitors the number of pipette tips positioned in the tip trays and/or the level of waste in the solid waste bin. The instrument inventory management system is frequently an automated real-time instrument inventory management system. The instrument inventory management system also frequently comprises (1) a camera and an associated image processor, and/or (2) a proximity sensor and a barcode reader. The camera is often statically mounted in optical communication with at least one instrument consumable, but is frequently mounted on the robot arm such that it can be movably positioned throughout the instrument.

Two or more container holders (e.g., 3 container holders, or more) are frequently positioned on the periphery of the rotatable platform. Each container holder is rotatable around an individual secondary axis of rotation that is different than the secondary axis of each other container holder. In addition, vortexing of sample containers or reaction vessels frequently comprises orbital mixing. The orbital mixing comprises rotation of the rotatable platform circularly around the central axis together with rotation of the two or more container holders circularly around their secondary axes in a direction opposite of the rotation of the rotatable platform.

In one embodiment the processing station comprises a power line communication system.

The different shaped containers often comprise containers having differing widths, heights, diameters, and/or a combination thereof.

In one set of embodiments the data scanning mechanism comprises a barcode scanner. The barcode scanner is often utilized to, in addition to barcode scanning, determine the centerline and/or position of a barcode on a sample container or reaction vessel.

A process of automated mucoid strand detection and elimination from a sample aspiration device is also provided herein, comprising: (a) placing the sample aspiration device in a vessel containing a biological sample, wherein the vessel has closed bottom portion and an open top portion; (b) aspirating at least a portion of the sample; (c) withdrawing the sample aspiration device from the sample; (d) while the sample aspiration device is withdrawn from the sample, imaging at least a portion of the sample aspiration device and processing the imaging results to detect whether a mucoid strand is present on the sample aspiration device, wherein if a mucoid strand is detected, the sample is dispensed into the vessel and steps (a)-(d) are repeated until a mucoid strand is not detected. Often, if a mucoid strand is detected in step (d), the repeated step (b) is performed in a different portion of the container versus the initial or previous step (b). Also often step (c) comprises separating the sample aspiration device from the fluid remaining in the vessel.

In frequent embodiments the sample aspiration device is imaged with machine vision and the imaging processing occurs automatically without manual user input. Often imaging comprises imaging of at least the tip of the sample aspiration device.

The sample aspiration device often comprises a pipette tip positioned operably on a pipettor. Frequently, the pipettor is capable of performing capacitive liquid level detection and/or reverse capacitive liquid level detection.

In the most frequent embodiments the vessel is vortexed prior to step (a). a mucoid strand is detected, the sample is vortexed prior to repeating any process steps after dispense of the sample into the vessel.

In frequent embodiments steps (b) and (c) occur with the sample aspiration device positioned directly over the open top portion of the vessel.

A system for automated real-time inventory control of consumables within a biological sample handling or assay instrument is also provided herein, comprising: (a) one or more consumable types, each comprising more than one unit of the consumable; (b) an image collection device in optical communication with the one or more consumable types; and (c) an image processor, wherein the image collection device captures an image of the one or more consumable types and the image is automatically processed to determine the unit number, position, and/or presence or absence of the one or more consumable types. In a frequent embodiment the one or more consumable types are backlit from a position opposed to the location of the image collection device, such that the image collection device is in optical communication with the resulting backlighting illumination.

In one embodiment the consumable type is a pipette tip, a sample container, a reaction vessel, an input rack, an output rack, or a reagent.

In a frequent embodiment the image collection device is statically mounted in optical communication with the one or more consumable types. Also frequently the image collection device is movably mounted in optical communication with the one or more consumable types. In such embodiments the image collection device is often mounted on a robot arm.

In occasional embodiments the image processor is comprised within the image capture device. In other embodiments, image processing occurs in a device external to the image capture device, for example, a computer or computing mechanism.

In one embodiment the system comprises two or more image capture devices and image processors. Each of these two or more image capture devices is frequently in optical communication with at least one consumable type. Often each of the two or more image capture devices is in optical communication with two or more consumable types. In frequent embodiments the image capture device is positioned in optical communication with a waste bin wherein the image collection device captures an image of the waste bin and the image is automatically processed to determine the presence and/or remaining capacity of the waste bin. Also often the image capture device captures an image of the one or more consumable types and the waste bin in a single image.

In certain embodiment the system further comprises an operator notification protocol, wherein the operator is notified in real-time about the inventory of the one or more consumable types detected during imaging and image processing.

The system also frequently comprises a power line communication system.

A high throughput, random access automated instrument for processing biological samples is also provided herein, comprising: (a) a sample processing station; (b) a system for automated real-time inventory control of consumables; (c) a sample input bay configured to hold one or more sample input racks; (d) a sample output bay configured to hold one or more sample output racks; (e) a power line communication system; (f) a waste bin; (g) a consumable inventory bay; (h) a robot arm having a pipettor operably positioned thereon; (i) a pick-and-place mechanism for moving a container within the instrument; and (j) a user interface.

In a frequent embodiment the instrument comprises an automated system for identifying and processing a failed sample processing such that the failed sample is identifiable to a user of the instrument and/or a downstream automated molecular instrument.

In another frequent embodiment the automated system for identifying and processing a failed sample processes the failed sample in a manner that does not affect the overall throughput speed of the instrument.

In one frequent embodiment the instrument further comprises a printer module for use in printing a barcode on a reaction receptacle or a sample container. The printer module is often in data communication with a barcode reader such that a barcode read by the barcode reader can be reproduced by the printer module.

An automated instrument for processing or analysis of a sample is also provided herein comprising: (a) a barcode reader; and (b) a printer module in data communication with the barcode reader, wherein the processing or analysis of the sample comprises automated transfer of at least a portion of the sample from a first receptacle to a second receptacle, and wherein the barcode reader scans a barcode present on the first receptacle, information associated with the barcode is transferred between the barcode reader and the printer module, and the printer module prints a barcode on the second receptacle. The first receptacle frequently comprises a sample container and the second receptacle comprised a reaction vessel. Moreover, the barcode printed on the second receptacle is often the same barcode present on the first receptacle.

In another frequent embodiment the barcode printed on the second receptacle is a different barcode versus the barcode present on the first receptacle. Often the information associated with the barcode printed on the second receptacle comprises the information associated with the barcode present on the first receptacle and further comprises additional information.

Methods of using the disclosed instruments, mucoid detection processes, and systems to process and/or analyze samples are also frequent embodiments of the present disclosure.

These and other features, aspects, and advantages of the present invention will become apparent to those skilled in the art after considering the following detailed description, appended claims and accompanying drawings.

DETAILED DESCRIPTION OF THE PREFERRED EMBODIMENTS

Figure 1:
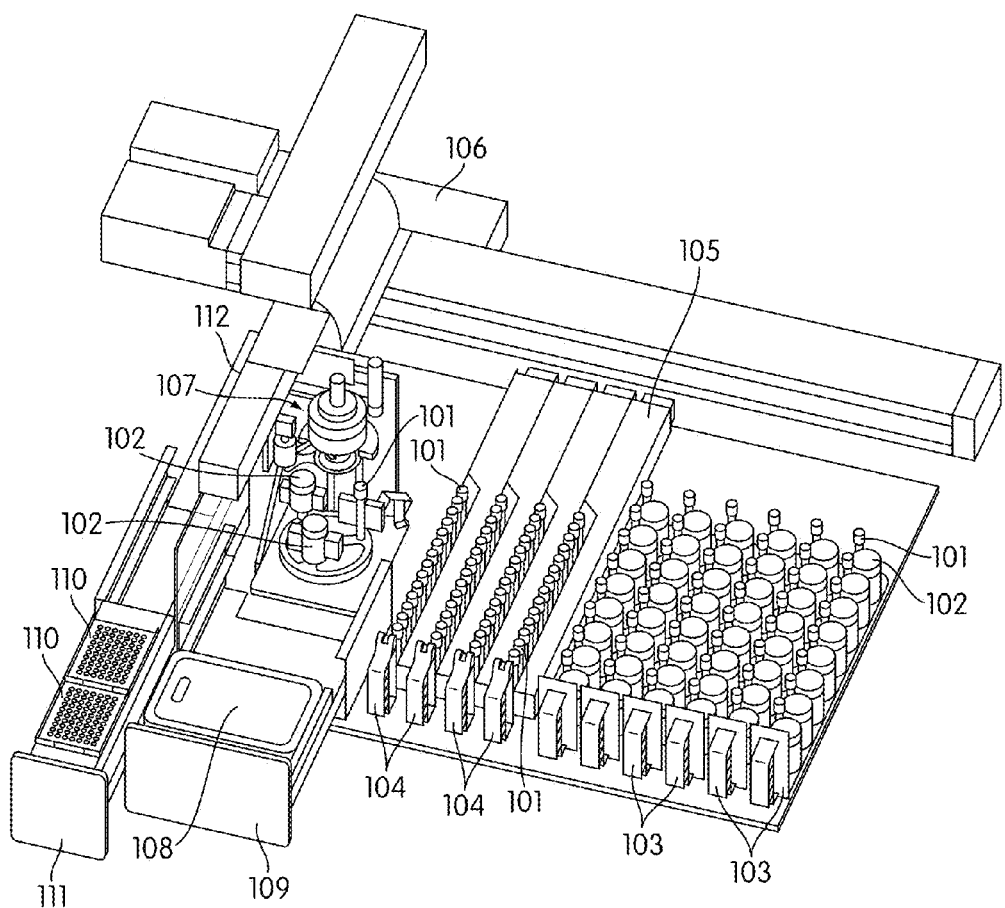
FIG. 1 provides a depiction of one embodiment of a sample processing instrument of the present disclosure.

Unless defined otherwise, all terms of art, notations and other scientific terms or terminology used herein have the same meaning as is commonly understood by one of ordinary skill in the art to which this disclosure belongs. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. All patents, applications, published applications and other publications referred to herein are incorporated by reference with regard to each issue for which they are cited, and related issues. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

As used herein, "a" or "an" means "at least one" or "one or more."

As used herein, a "sample" or "biological sample" refers to a biological specimen such as any tissue or polynucleotide-containing material obtained from a human. Biological samples in accordance with the invention include peripheral blood, plasma, serum, bone marrow, urine, bile, mucus, cerebrospinal fluid, stool, exosomes, biopsy tissue including lymph nodes, respiratory tissue or exudates, gastrointestinal tissue, cervical swab samples, semen or other body or cellular fluids, tissues, secretions, or materials. Often biological samples are diluted or contained within a vessel containing diluents, transport media, preservative solution, or other fluids. As such, a biological sample of the present invention is intended to encompass a biological sample contained within a diluent, transport media, and/or preservative or other fluid intended to hold a biological sample.

As used herein, "reaction vessel" refers to any container, tube, test tube, vial, or other vessel configured to hold fluid and can be utilized in a molecular, microbiologic, immunologic, or other diagnostic biological assay. One preferred aspect of reaction vessels of the present invention is the ability to withstand a heated (e.g., between 35° C.-90° C.) incubation without deforming or leaching chemicals into the sample contained therein. One exemplary reaction vessel is the APTIMA® tube (Gen-Probe Incorporated, San Diego, Calif.).

As used herein, "assay instrument," "automated assay instrument," and "molecular assay instrument" refer to a biological sample analyzer capable of evaluating a biological sample and rendering a result. Overall, any instrument capable of performing a hybridization assay, amplification assay, sequencing assay, or immunoassay is included in this definition. A couple of exemplary assay instruments include TIGRIS® and PANTHER® instruments (Gen-Probe Incorporated, San Diego, Calif.).

As used herein, "machine vision" refers to a branch of engineering that uses computer vision in the analysis of images to extract data for controlling a process or activity. See, e.g., A. Hornberg, HANDBOOK OF MACHINE VISION (Wiley-VCH Verlag GmbH & Co. KGaA, Weinheim 2006); C. Steger et al., MACHINE VISION ALGORITHMS AND APPLICATIONS (Wiley-VCH Verlag GmbH & Co. KGaA, Weinheim 2008). A machine vision process is targeted at recognizing the actual objects in an image and assigning properties to those objects—understanding what they mean.

As used herein, "orbital mixing" refers to a motion that induces a stirring effect in a liquid-filled reservoir without requiring a mixing utensil such as a spoon, magnetic particle, or similar. In an exemplary embodiment of orbital mixing the reservoir is subjected to extraneous forces, such as centripetal force and/or centrifugal force, which induce a stirring effect in the liquid contained therein. In the present sample processing instrument orbital mixing of sample containers and reaction vessels occurs in the sample processing station where, for example, one or more sample container(s) and/or a reaction vessel(s) are positioned on the periphery of the rotatable platform. Orbital mixing is achieved whereby the rotatable platform rotates in one direction around a central axis and the sample container(s) and/or a reaction vessel(s) rotate concurrently in an opposite direction than the rotatable platform, each about an individual axis that is different than the central axis of the rotatable platform as well as the axis of each other sample container or reaction vessel.

As used herein, "robot arm" refers to an electromechanical device that translates a payload (e.g., a pipettor, a pick-and-place claw, a camera, a sensor, a capper/decapper, etc.) in the X, Y, and/or Z directions. A frequent embodiment provides a robot arm capable of movement in the X, Y, and Z directions.

As used herein, "mucoid" refers to any viscous material, such as a viscous colloid or a viscous fluid.

As used herein, "power line communication," "power line communication system," or "PLC" refers to use of power lines in the instrument to transmit data signals throughout the instrument. See, e.g., POWER LINE COMMUNICATIONS: THEORY AND APPLICATIONS FOR NARROWBAND AND BROADBAND COMMUNICATIONS OVER POWER LINES (H. C. Ferreira et al. eds., John Wiley & Sons Ltd. 2010). Power line communications systems operate, for example, by imposing a modulated carrier signal on the wiring system.

Certain biological samples can be run on a molecular assay directly without any sample processing. However, biological samples such as liquid based cytology (LBC) samples often require processing prior to assay. Numerous other biological samples often require processing prior to assay, including cell samples, tissue samples, stool samples, mucus samples, semen samples, cerebrospinal fluid samples, blood samples, bone marrow samples, serum samples, urine samples, bile samples, respiratory samples, sputum samples, and exosome samples, among others. Often, it is the particular assay to be run that requires particular sample processing while permitting assay of a variety of sample types. For example, human papillomavirus (HPV) assays, *Chlamydia* assays, gonorrhea assays, human metapneumovirus assays, *mycoplasma pneumoniae* and *chlamydophila pneumonia* assays, *bordetella pertussis* assays, *clostridium difficile* assays, human metapneumovirus assays, and Parainfluenza virus assays, prostate cancer assays, benign prostatic hyperplasia assays, among others, may be performed on a variety of sample types, but each sample type may require particular processing prior to being able to run the assay. Also frequently, the type of assay to be run may dictate whether and/or what sample processing is required prior running an assay. For example, nucleic acid assays such as hybridization assays, amplification assays, and sequencing assays often require sample processing prior to conducting the assay. Protein assays such as sequencing assays and immunoassays also may require sample processing prior to conducting an assay. Although pre-assay processing LBC samples is one preferred use of the present invention, the present invention is useful for conducting accurate and rapid sample processing of any of the above sample types for at least the assay types noted above.

Figure 2:
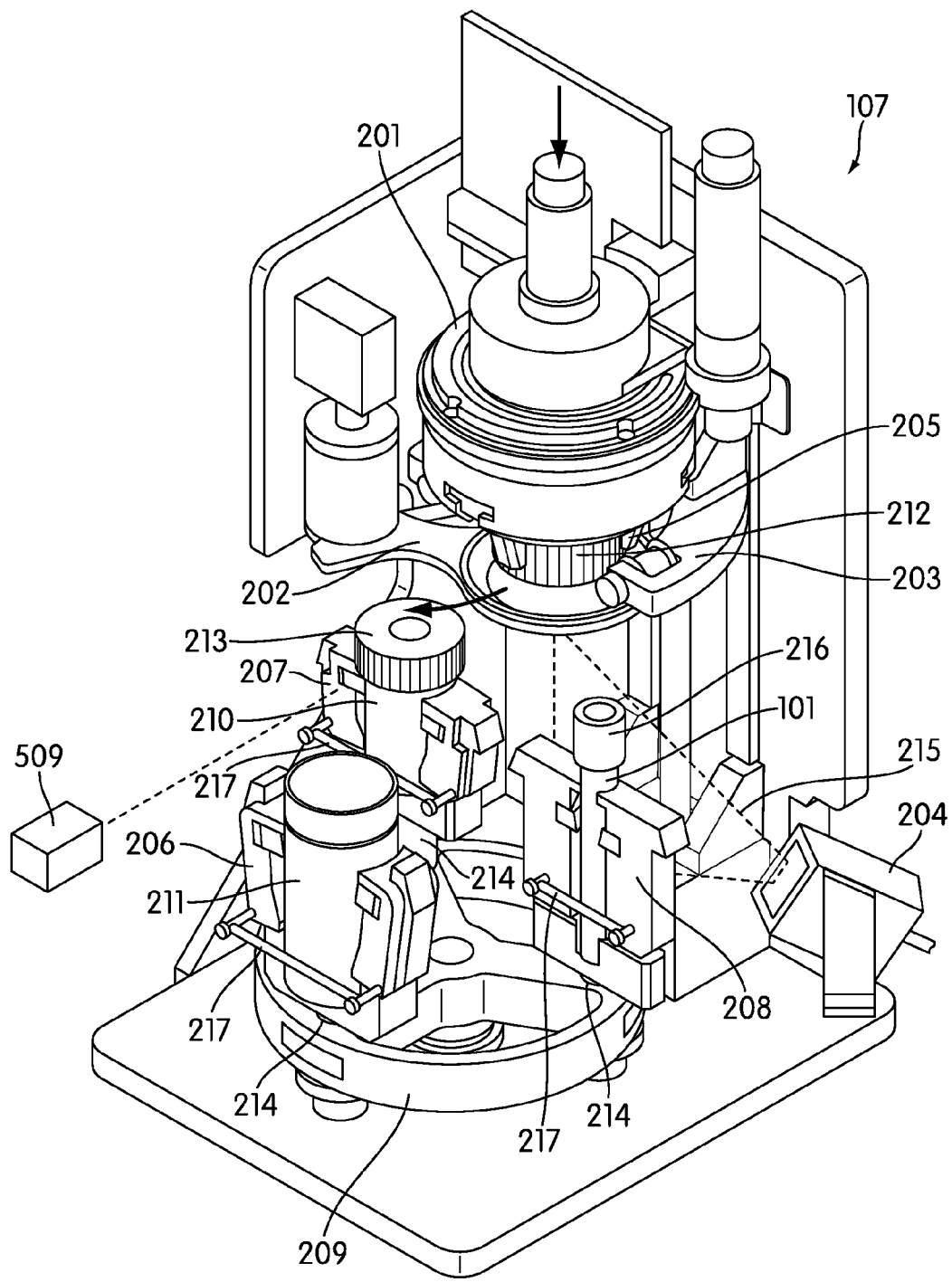
FIG. 2 provides a perspective view of one embodiment of the sample processing station of the sample processing instrument of the present disclosure.
Figure 3:
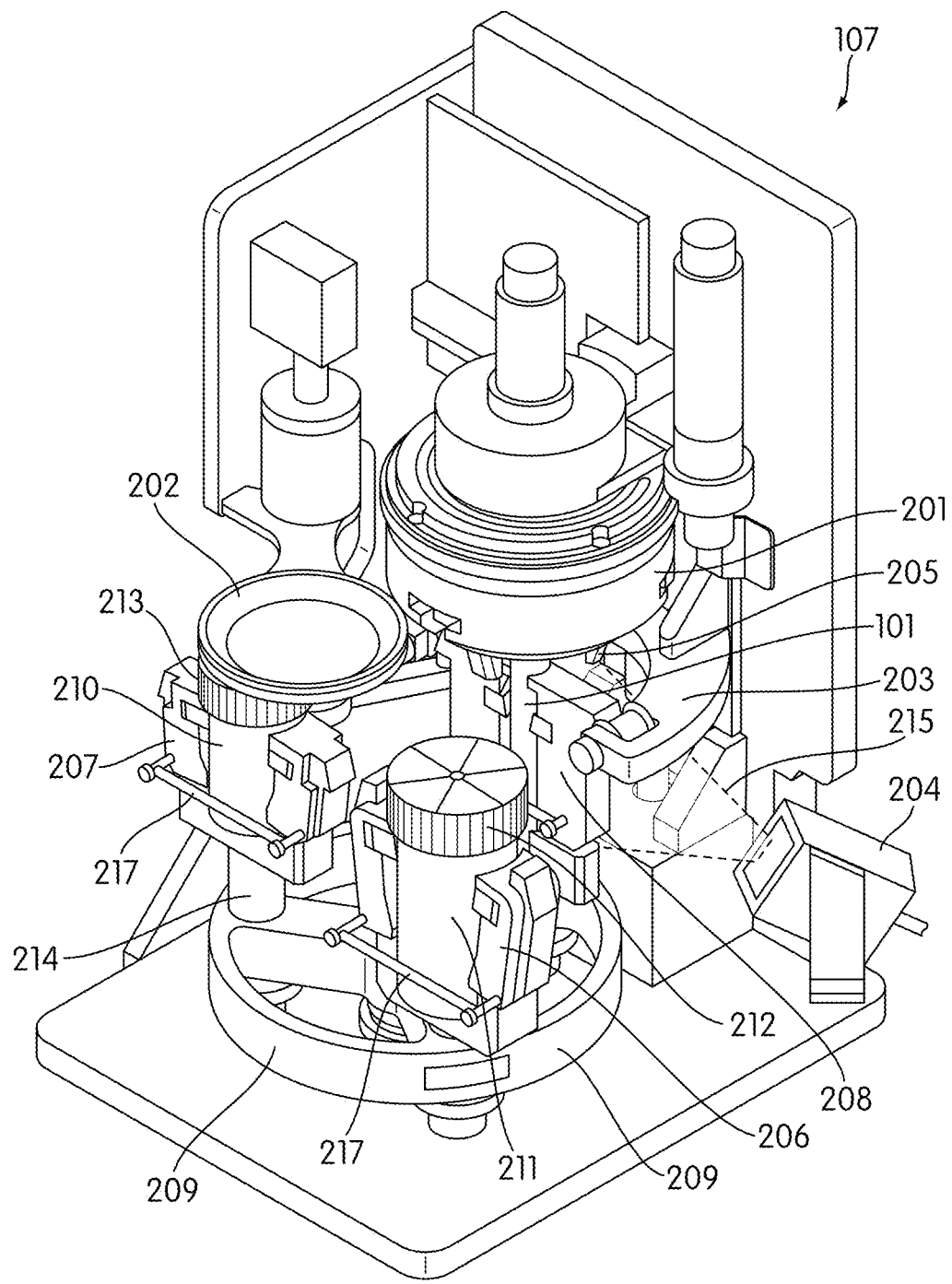
FIG. 3 provides another perspective view of one embodiment of the sample processing station of the sample processing instrument of the present disclosure.

Referring to FIG. 1, the sample processing station (107) is incorporated in an automated instrument including one or more input racks (103), one or more output racks (104), a robotic arm (112, 407, 408), a sample pipettor (406), one or more incubators (105), and an embedded controller. In such an embodiment, the robotic arm (112, 408) moves sample containers (102) and reaction vessels (101) between the input racks (103), the sample processing station (107) and the output racks (104). Each of these components is preferably incorporated within an instrument housing. The sample pipettor (406) transfers specimens from sample containers (102), such as liquid based cytology (LBC) specimen containers to reaction vessels (101) (e.g., APTIMA® sample tubes available from Gen-Probe Incorporated, San Diego, Calif.) while also performing liquid level detection and reagent dispensing. The sample processing station (107) preferably is configured to hold the sample containers (102) and reaction vessels (101), perform barcode reading (FIG. 2, 204), barcode positioning, specimen mixing, and capping/uncapping of the sample container and reaction vessel. One or more incubators (105) are frequently incorporated into the instrument and are occasionally, such as in the depicted embodiment, adapted to hold one or more sample output racks (104) and utilized to incubate the sample directly within the reaction vessel. Often LBC samples, such as samples collected in a SUREPATH® (Becton Dickinson, Inc., Franklin Lakes, N.J.) specimen collection containers (210), often require reagent addition and heated incubation prior to further processing such as a molecular assay. Other LBC sample types, such as those collected in a THINPREP® (Hologic, Inc., Bedford, Mass.) device (211), often may not require incubation. When heated incubation is not required as part of sample processing the one or more incubators in the instrument, if configured to hold an output rack, may act as an output queue with temperature control turned off. The instrument also frequently incorporates an embedded controller that manages and processes system-wide activities by delegating specific tasks to instrument sub components or modules. Exemplary system activities include capping/decapping collection and reaction vessels, vortexing, pick-and-place of collection and reaction vessels, pipetting, waste reservoir monitoring, monitoring consumable inventory, monitoring sample queues, maintaining run logs, monitoring process controls, monitoring system alarms, etc.

Though the instrument is often self-contained, accessories for use outside the instrument housing can be utilized for the convenience of the operator and sample processing efficiency. Accessories of this type include, for example handheld barcode readers, uninterruptible power supplies, and communication port (e.g., Ethernet, USB, eSATA, FIREWIRE®, Wi-Fi, BLUETOOTH®, THUNDERBOLT®, RS-232, RS-485, etc.) compatible instrumentation useful for, for example, updating system configuration files, transfer of systems logs, transfer of sample information, etc.

The instrument may also incorporate a software user interface. In one embodiment the user interface incorporates an integrated touch screen used for operator input, instrument control, status monitoring, and display of sample tracking information. Data input means such as USB ports are frequently incorporated, for example, to facilitate system configuration file updates, downloading sample tracking data/run logs and for connection of an external mouse and keyboard.

Figure 9:
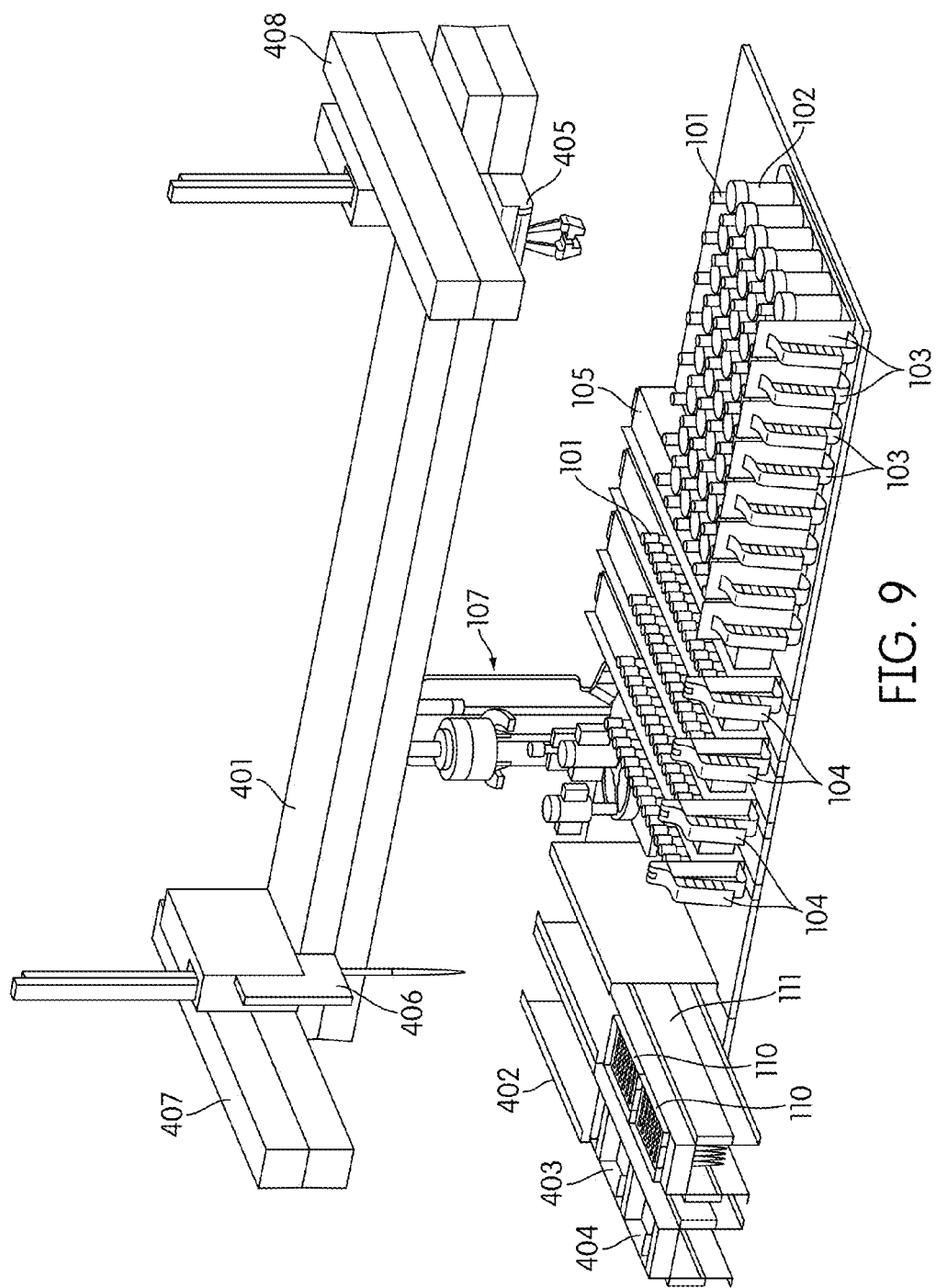
FIG. 9 provides a depiction of another embodiment of a sample handling instrument of the present disclosure.
Figure 10:
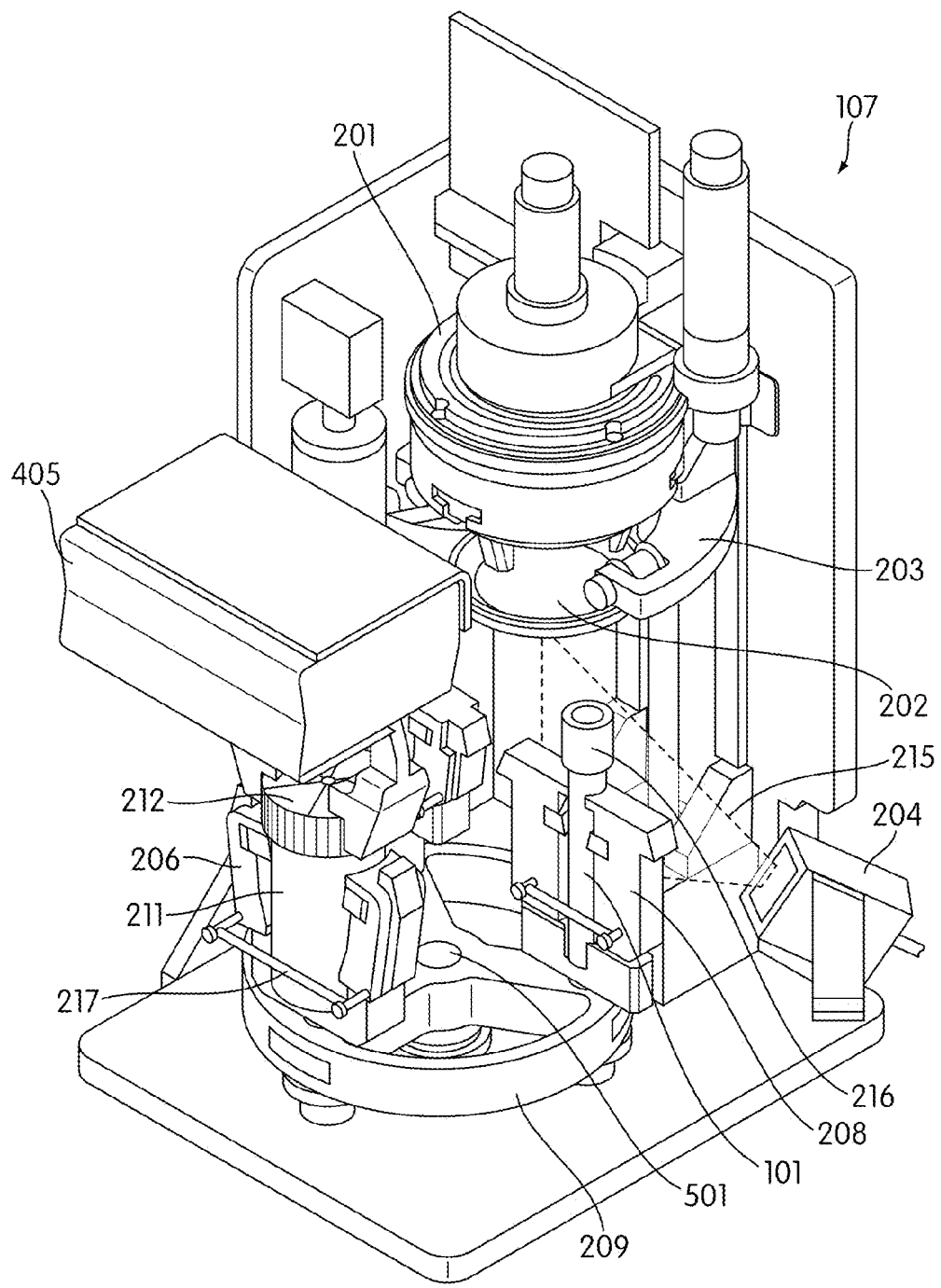
FIG. 10 provides a perspective view of an examplary sample processing station, including a pick-and-place mechanism grasping a sample container positioned in the service position.

The instrument also generally incorporates a hardware user interface where a user can access the sample input area, the sample output area, and the consumable area. For example, in one embodiment the instrument includes two or more cabinets or drawers on the front of the instrument to access these areas. In a preferred embodiment, the instrument incorporates two doors and two drawers, where one drawer (111) can be configured to contain the instrument consumables, such as pipette tip trays (110), sample processing reagents, and another drawer (109) can be configured to contain the waste container (108). Although FIG. 1 depicts only pipette tip trays (110) in consumable drawer (111), one of skill in the art would understand that additional or replacement containers can be included in such a drawer to contain sample processing reagents. In addition, although the solid and liquid waste container (108) is depicted as a single container, one of skill in the art would understand that the waste container (108) may preferably be partitioned or separated into two independent waste storage areas, one for solid waste (e.g., used pipette tips) and the other for liquid waste (e.g., discarded sample). FIG. 9, for example, depicts such an arrangement, including a waste container drawer (402), a liquid waste container (403) and a solid waste container (404).

Turning back to FIG. 1 shows an embodiment where a cabinet can be configured to hold one or more output racks (104), which can slide into the instrument incubators (105). These output racks (104) act as output queues for the system. Also in this embodiment, another cabinet can be configured to hold one or more input racks (103) (also referred to herein as sample racks).

Since the instrument is configured to handle a variety of sample types, including samples collected in different shaped collection vessels (e.g., 210, 211—collectively 102), in a particularly preferred embodiment this cabinet is configured to hold multiple types of sample racks. For example, in one embodiment the cabinet is configured to hold sample racks (103) containing THINPREP® and/or SUREPATH® sample containers (211, 210, respectively). In a related embodiment each sample rack (103) is configured to hold a single type of specimen such that if two racks are present one rack may contain only THINPREP® specimen containers (211), whereas the other rack contains only SUREPATH® specimen containers (210). In a separate preferred embodiment, each sample rack (103) is configured to hold two or more different shaped sample vessels, for example a sample rack may hold both THINPREP® and SUREPATH® sample containers. In this embodiment the sample rack (103) is often configured to hold SUREPATH® sample containers (210) (including the corresponding reaction vessels (101)) on one side, and THINPREP® sample containers (211) (including the corresponding reaction vessels (101)) on the opposite side. In use, the sample rack can hold SUREPATH® sample containers and then if flipped upside down, it can hold THINPREP® sample containers.

Additional features may optionally be included as part of each cabinet or drawer, such as indicator lights that can provide visual feedback to the user regarding the current state of the racks, consumables, or waste containers in the instrument. For example, the indicator lights can indicate to the user whether a particular rack is being processed, and therefore cannot be accessed. In contrast, the lights can also indicate to the user when it is safe to remove a rack that has been processed to make room for another sample rack. Similar indicator lights can be included for the sample output racks and the consumable drawer. In one embodiment, when the drawers are open, the indicator lights are visible to the user for visual assistance during interventions.

An exemplary input rack is configured to hold both a sample container and a reaction vessel. This sample rack is preferably configured to hold multiple pairs of sample containers and reaction vessels, such that they are incorporated in a one-to-one ratio, in an alternating fashion. In this embodiment the primary action required by the user, after verifying instrument consumable levels, to begin sample processing is to load the rack with pairs of sample tubes and reaction vessels and insert the rack into the instrument for sample processing to occur.

Figure 7:
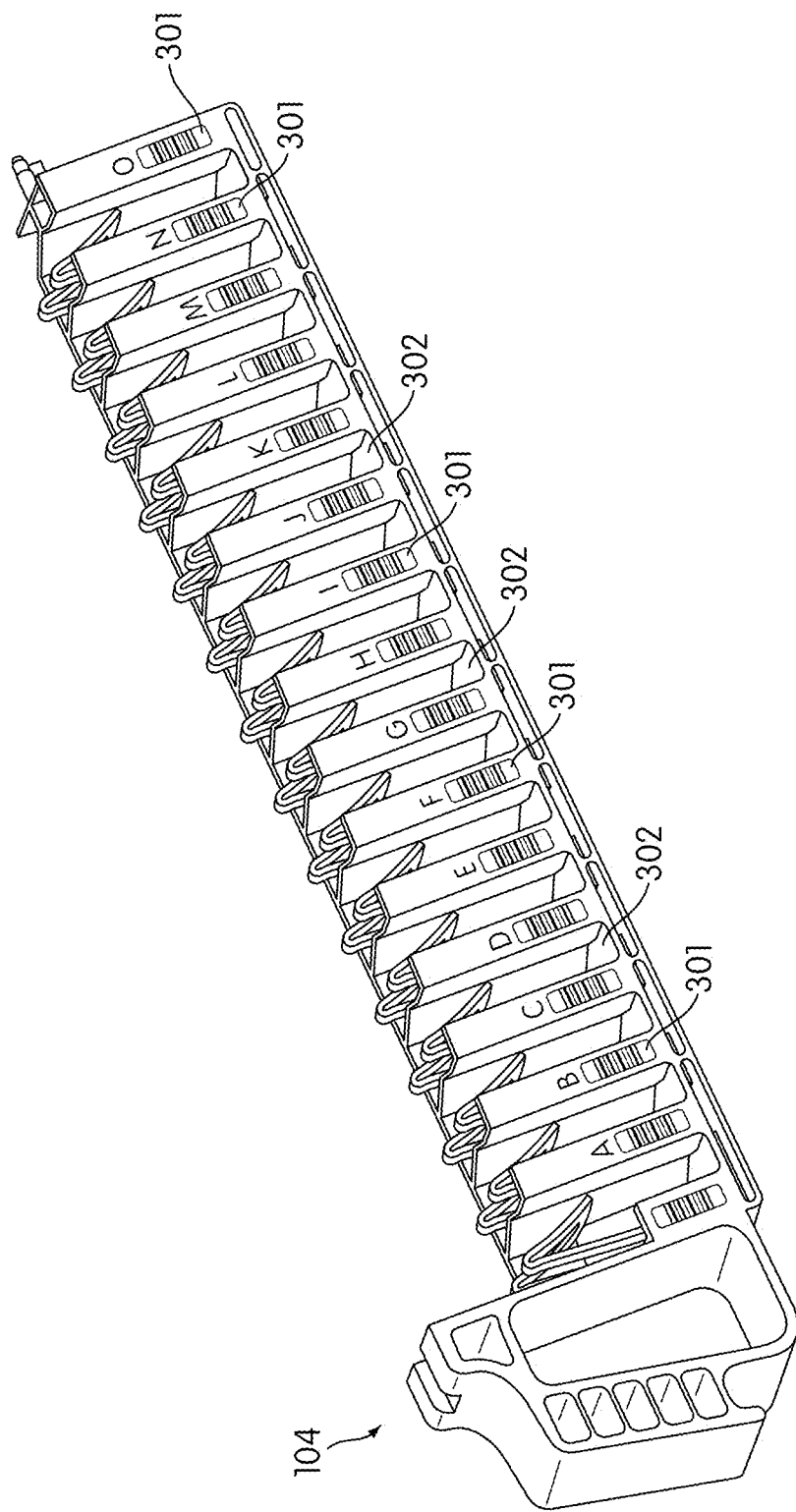
FIG. 7 provides a perspective view of an exemplary output rack.
Figure 8:
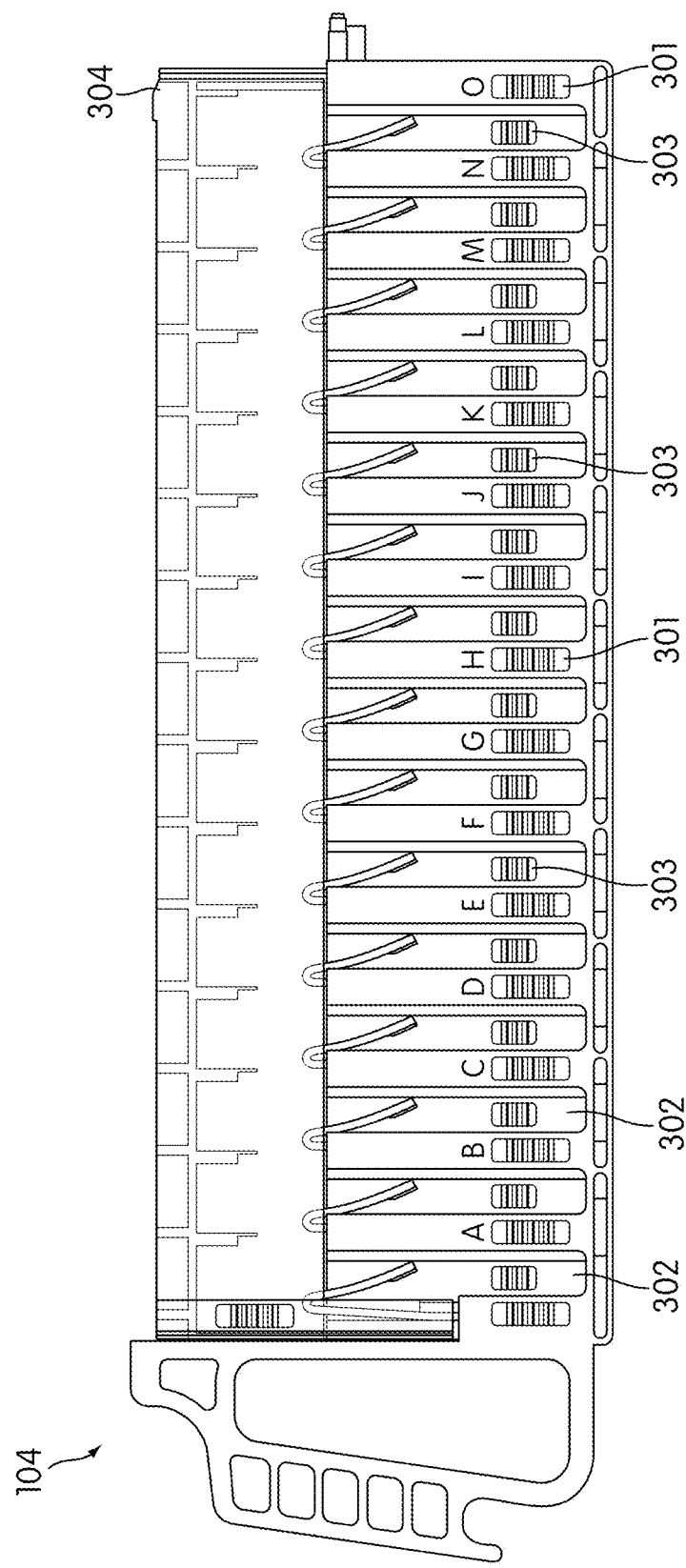
FIG. 8 provides another perspective view of an exemplary output rack including a cover.

With reference to FIGS. 7 and 8, an exemplary output rack (104) is depicted that is configured to hold a plurality of reaction vessels. The instrument automatically processes the reaction vessels from the input rack (103) to the output rack (104), where the user can retrieve the output rack to be run in an assay. In a preferred embodiment the output rack is configured to be operable in an automated instrument capable of performing a molecular assay. In such an embodiment the user retrieves the rack containing processed samples in the reaction vessels and, with or without any additional required activities such as attaching a cover to the rack, places the rack in the automated molecular assay instrument to perform a desired assay. In a less preferred embodiment, the reaction vessels in the sample output rack are manually transferred to a rack configured to be operable in an automated molecular assay instrument.

The output rack (104), for example, itself is adapted to receive and hold a plurality of receptacles, which, in certain embodiments, may comprise tubular containers, such as test tubes or APTIMA® transport tubes. An exemplary output rack is described in U.S. Patent Application Publication No. 2010-0288061. The gap between each pair of adjacent divider walls in the output rack (104) defines a sample receptacle pocket (302), or receptacle-receiving area, for receiving an individual receptacle. In one embodiment, pocket-identifying indicia, such as barcode (301), is provided on the divider walls (110) adjacent each pocket (302). The indicia, which may also include an alphanumeric identifier, e.g., "A", "B", "C", etc., uniquely identifies each pocket (302). A machine readable label, such as "empty pocket" barcode (303), may be provided within each pocket (302), on the inner side of the pocket 302 to uniquely identify each pocket (302) and to indicate when a receptacle is not present in the pocket 302.

In certain embodiments the output rack comprises a microtiter tray, such as a 96 well plate. In such embodiments sample can be introduced to the microtiter tray or output rack directly from the sample tube. Often, however, when incubation is required an intermediate tube is utilized for incubation such that sample is transferred to the intermediate tube from the sample tube, then transferred again from the intermediate tube to the microtiter tray after incubation.

In one frequent embodiment, specimens are tracked within the instrument by placing matching barcodes on both the sample container and the reaction vessel. For example, an onboard barcode scanner (204) reads the tube barcodes once each tube is placed in the sample processing station. Such a barcode reader is often able to locate the positioning of the barcode on the sample container or reaction vessel by, for example, identifying the location of one or more edges of a label positioned on the container or vessel and deducing the location of the barcode on the label between the identified edges, or positioned a certain distance from a particular edge. All system process controls, tube barcodes, time/date stamps, user information, and system status are frequently stored in an onboard tracking system that is queryable via sample container or reaction vessel barcode. Frequently, the user can manually enter an identifier associated with the barcode by use of an instrument touch screen or through the use of an optional handheld barcode scanner to perform a query. The system software can be adapted to monitor the overall system status, reagent and supply inventories, processed specimen records, and maintenance. In another embodiment samples are tracked within the system through the use of radio-frequency identification (RFID). In such an embodiment, sample-, assay-, reagent-, system status-, user-, time/date stamp-, and/or instrument-related information can be written or re-written to an RFID tag and tracked and/or updated through sample processing and beyond.

In one embodiment, the instrument incorporates a robotic arm (112, 408) that is translatable in the X, Y, and Z planes to move sample containers and reaction vessels between modules (e.g., the sample processing station) in the instrument. In a preferred embodiment, the robotic arm (112, 408) incorporates an air-based pipettor system to dispense samples and reagents into reaction vessels.

In one embodiment the pipettor system is provided as part of an XYZZ robotic system (106), including an integrated air-pipettor (406) and a tube gripper (405). Most frequently, the pipettor and tube gripper are incorporated on the same robotic arm (405), but each has an independently operable Z-axis. This system frequently has common XY axes and 2 independent Z axes to service the pipettor and tube gripper. This system also frequently comprises a cartesian system with belt driven X, Y and gear driven Z axes. The motors in this system frequently have rotary encoders, home and limit sensors. In a frequent embodiment, the robotic arm can move to any point on the instrument deck within about 2 seconds or less.

One example of a contemplated pipettor head (406) is a fully integrated OEM module (available from Tecan Group Ltd., Männedorf, Switzerland) capable of dispensing volumes from 10-1000 uL with a CV of 0.75%. In such an embodiment the pipettor head is mounted a Z axis of the robotic arm. In a preferred embodiment the pipettor is compatible with Tecan disposable tips (e.g., 10 µl, 50 µl, 200 µl, 1000 µl, with or without filter), and is an air-based-pipettor that does not require tubing, valves, or syringes. The pipettor head frequently contains advanced on-board pump diagnostics, self-test, and error reporting. Moreover, a preferred pipettor has configurable liquid level detection with integrated pressure sensor (pLLD), is compatible with external capacitive liquid level detection hardware (cLLD), can provide real time streaming data from one or more pressure sensor(s) for process monitoring, and has a DiTi presence sensor and DiTi ejection mechanism.

The tube gripper module (405) is often responsible for pick-and-place of the sample containers and reaction vessels within the system. In one embodiment it is mounted to the secondary Z axis on the robotic arm. In a related embodiment, the gripper mechanism contains a cam disk that opens and closes the gripper when rotated CW/CCW. In this embodiment the cam disk is optionally driven by a small high torque DC gear motor or stepper motor. A variety of additional gripper mechanisms are also contemplated and known in the art.

In another preferred embodiment, such as that depicted in FIG. 9, the instrument includes two or more robotic arms (407, 408), each with a dedicated pipettor head (406) or tube gripper (405).

In one embodiment, samples are transferred from sample containers (102) to reaction vessels in a serial fashion. For example, an aliquot of a sample is taken from one sample container (102) and transferred to a reaction vessel (101). Thereafter another, different sample is taken from a different sample container (102) and transferred to another, different reaction vessel (101). An exemplary process for transferring and processing the sample in the sample processing station is described in detail below.

With regard to samples requiring reagent addition and a heated incubation as part of sample processing, in one embodiment onboard incubators (105) are capable of heating the output racks as a final processing step before they are removed from the instrument. In this embodiment, each output rack (104) generally contains a single type of sample—one that requires heated incubation or one that does not. The incubator modules (105) in this embodiment serve at least two functions—sample incubation and as an output queue for the system. Each incubator module (105) can be configured to contain 1, 2 or multiple slots, each capable of housing an output rack. In an exemplary embodiment the incubators use Kapton heater foil for heating and passive convection flow for cooling. A variety of other incubator configurations are similarly contemplated for use in the present invention, regardless of the configuration of the incubator, such as forced air convection, Peltier device heating, resistive heating, circulating heated gas or liquid, etc. In a particularly frequent embodiment, samples located in the incubator will remain at the temperature set point +/−2° C. at steady state. In a preferred embodiment, the incubators are surrounded by insulating material, such as foam insulation.

When samples are incubated in output racks, they are generally incubated in batches corresponding to the maximum number of positions on the output rack, or less. For example, 15 samples, or less, in a single rack may be incubated at one time. Of course, in practice, one of skill in the art would appreciate that the number of samples in an output rack can be more or less than 15 samples depending on the number of slots available in the rack and the number of samples to be processed.

Figures 1, 11:
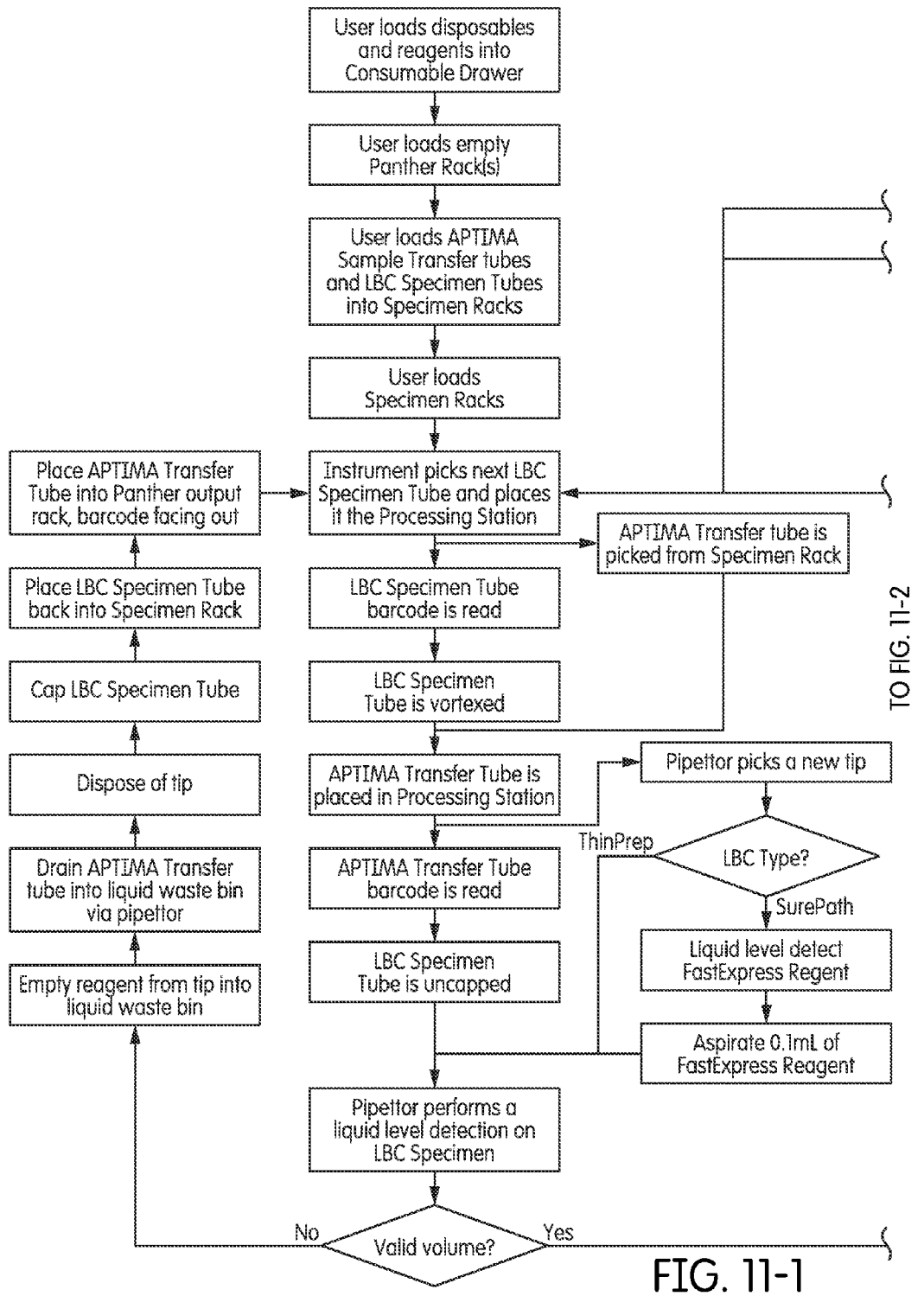
FIG. 11 provides one exemplary process flow for LBC specimen processing.
Figures 2, 11:
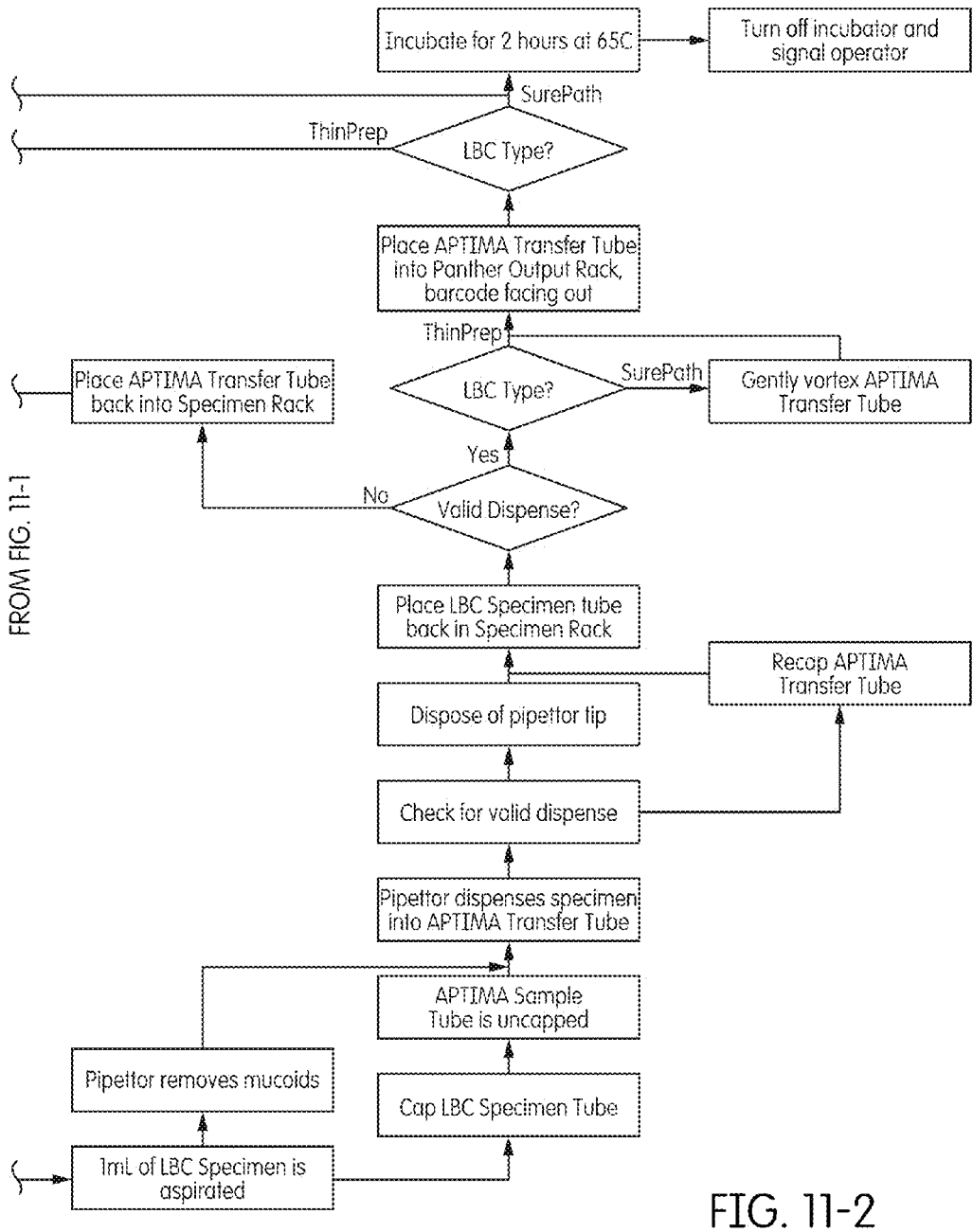

Another aspect of the instrument is that it permits a level of tuneability to provide automated sample processing according to protocols established by the manufacturer that established the particular assay to be run. These protocols are most frequently in accordance with regulatory guidelines and mandates. In a further aspect, the instrument permits automated sample processing according to protocols established by the manufacturer of the sample collection container. For example, LBC specimens can be processed in an automated fashion on the instrument in accordance with, for example, the THINPREP® or SUREPATH® protocol. In a frequent embodiment the sample racks are tagged (such as by way of an RFID tag, a mechanical flag, a unique machine readable identifier, machine vision, barcode readers, or another means) such that the instrument will recognize the type of sample present in the sample rack, and will automatically run the sample processing protocol that is specific for that type of sample. When multiple different sample racks are present, each containing samples requiring a processing protocol that is different from the protocol for any or each other rack, the instrument automatically processes the samples according to a rule set that balances throughput with time-to-next-result. For example, sample racks containing samples in THINPREP® containers can be loaded on the instrument for processing together with racks containing samples in SUREPATH® containers. FIG. 11 presents an exemplary process flow for preparing a combination of THINPREP® and SUREPATH® specimens in an instrument of the present disclosure.

Particularly preferred embodiments of a sample processing instrument of the present invention are depicted in FIGS. 14-17. In these embodiments a dedicated incubator (504) is provided for heated incubation of reaction vessels (101) that require incubation. In practice reaction vessels (101) will be placed in the incubator (504) by the pick and place mechanism (405, 507) after completion of processing in the sample processing station (107). After incubation is complete the reaction vessels (101) will be placed into an output rack (104) by the pick and place mechanism (405, 507). Depending on the throughput desired the number of output racks (104) can vary, for example, between 4 (FIG. 14) to 8 (FIGS. 15-17) output racks. However, one of skill in the art would appreciate that the number of output racks (104) utilized and/or space dedicated to output rack (104) use can vary to be less than 4 racks or more than 8 racks. In these embodiments the output racks (104) can be randomly populated with reaction vessels (101) that have been incubated and reaction vessels (101) that have not been incubated. The composition of sample types in the output rack (104) in these embodiments will frequently be determined by the type and number of samples processed by the laboratory at any particular time, without requiring sample batching as utilized in the output rack (104) incubating embodiments of the present invention.

In practice the embodiments of FIGS. 14-17 often utilize a steady-temperature incubator (504) such that when a reaction vessel (101) is placed in the incubator (504), incubation begins immediately. In such an embodiment, each reaction vessel holder (505) is heated to a particular predetermined temperature and maintained at that temperature regardless of whether a reaction vessel (101) is present or not. Alternatively, the incubator may be provided with cycling capability such that it will quickly heat to a predetermined temperature upon, or after, placement of a reaction vessel (101) in a reaction vessel holder (505). In another preferred embodiment the incubator is partitioned such that portions of the incubator may be individually heated, while other portions of the incubator (504) remain unheated. The partitions can comprise individual reaction vessel holders (505) such that each reaction vessel holder (505) is individually temperature controlled, alternatively, the partitions can comprise blocks of reaction vessel holders (505) such that 2 or more reaction vessel holders (505), for example about 5, 10, 15, 20, 25, 30, 35, 40, or more reaction vessel holders (505) are temperature controlled as a single unit. In any event, the system controller monitors the incubation timing of each reaction vessel (101) to ensure optimum sample processing in a time-efficient manner without operator intervention.

The embodiments depicted in FIGS. 14-17 show 130 reaction vessel holders in the incubator (504), however the number of reaction vessel holders (505) in the incubator (504) can vary over a large range, for example more or less than 130, depending on the throughput desired and the incubation time required. For example, for an exemplary incubation time of 2 hours and an individual sample processing time of one minute, a preferred embodiment incorporates at least about 120 reaction vessel holders (505). In this example a reaction vessel (101) can be introduced to the incubator (504) every minute over the course of 120 minutes such that the first introduced reaction vessel (101) completes its incubation, and can be removed from the incubator (504) to the output rack, at about the same time the last of the 120 reaction vessel holders (505) is filled. This always leaves an open spot for a new reaction vessel (101) to be introduced to the incubator (504), while maximizing throughput, but minimizing the space occupied by the incubator (504). In practice, such an embodiment will often include additional reaction vessel holders (505) in the incubator in case the pick and place mechanism is occupied with other duties, there are no spaces available in the output racks (104), or the system overall is occupied, at the time the initial incubation is complete. If the incubation time is less than 2 hours the number of reaction vessel holders (505) can be correspondingly decreased to maximize throughout. Correspondingly, if sample processing time is decreased to less than one minute it is often preferred to provide additional reaction vessel holders (505) in the incubator (504) such that a reaction vessel (101) can be placed in the incubator (504) at any time the initial sample processing in the sample processing station (107) is complete.

FIGS. 14-17 also depict an alternative configuration of the solid waste bin (108) and liquid waste container (502), in addition to the consumable area containing pipette tip trays (110) and reagent container (503).

Figure 14:
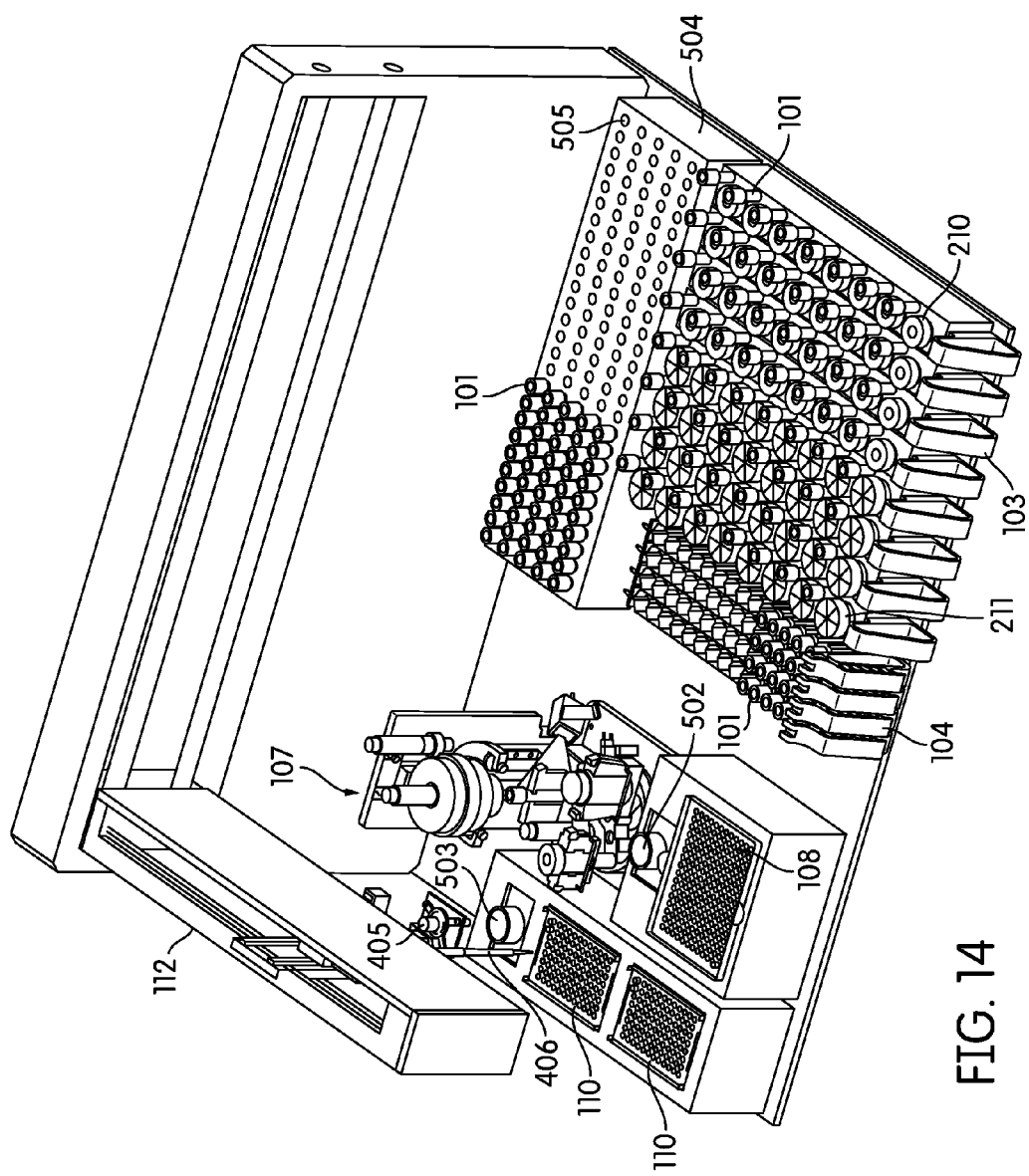
FIG. 14 provides a depiction of one embodiment of a sample handling instrument of the present disclosure.
Figure 15:
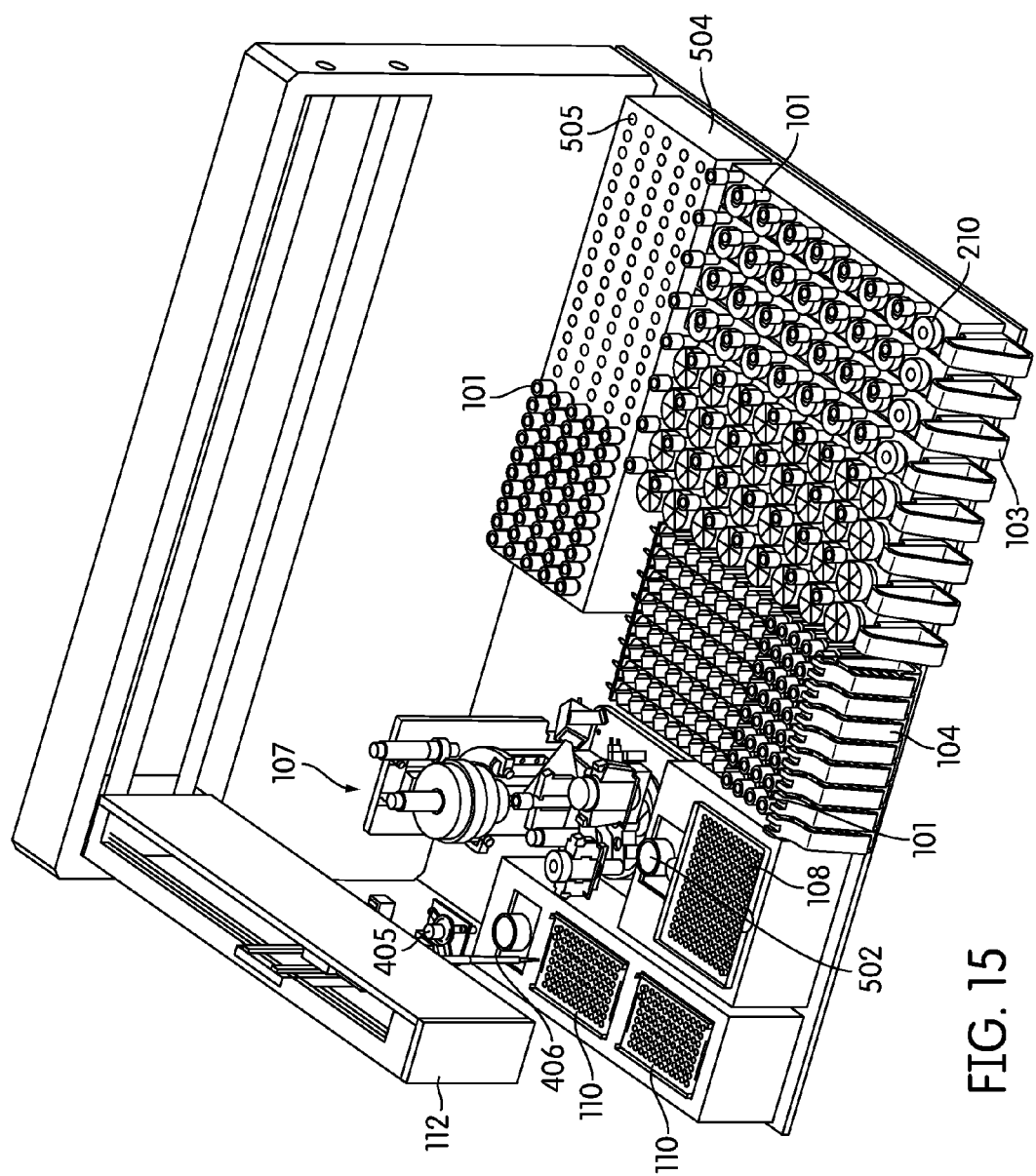
FIG. 15 a depiction of another embodiment of a sample handling instrument of the present disclosure.
Figure 16:
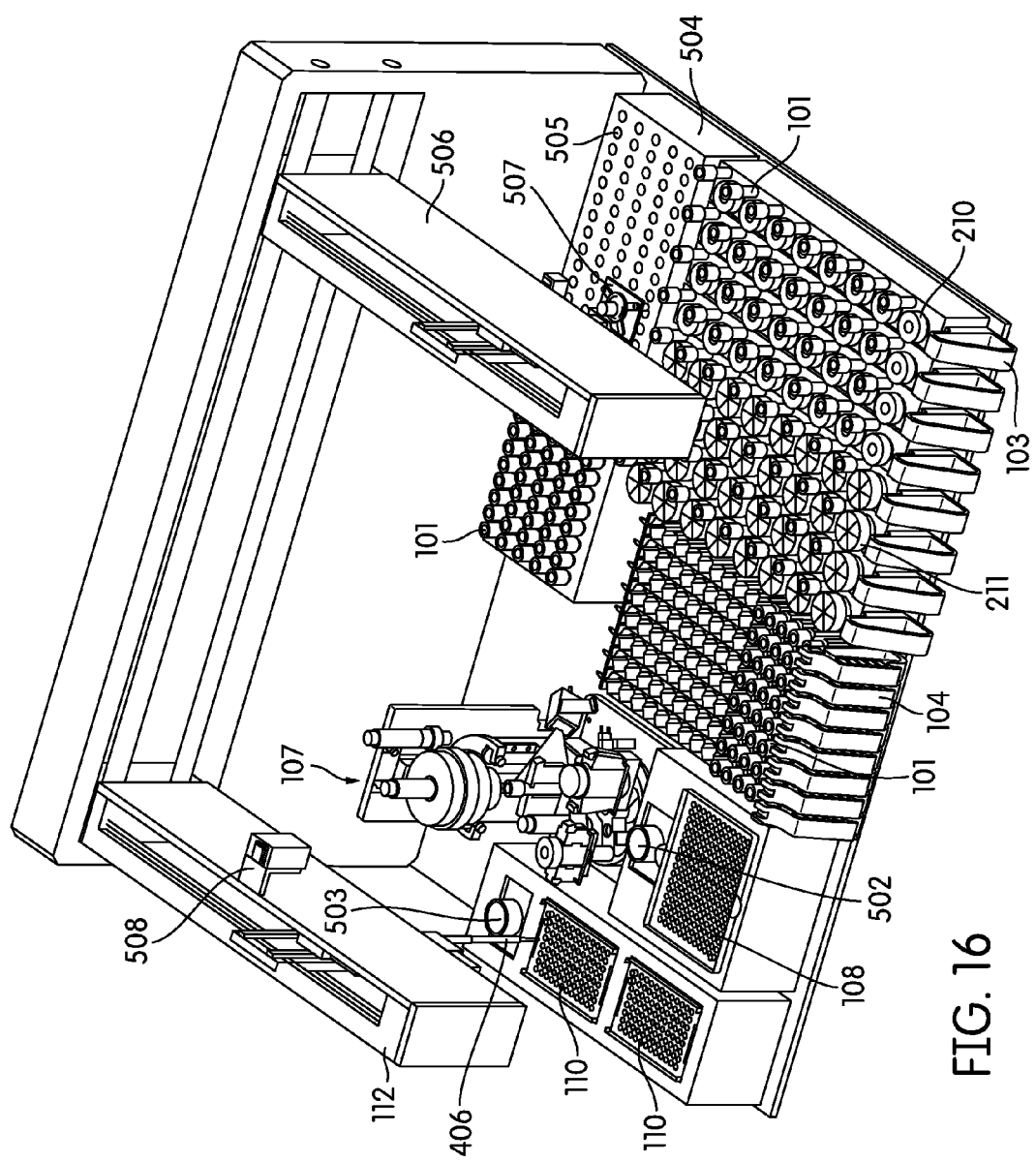
FIG. 16 a depiction of another embodiment of a sample handling instrument of the present disclosure.
Figure 17:
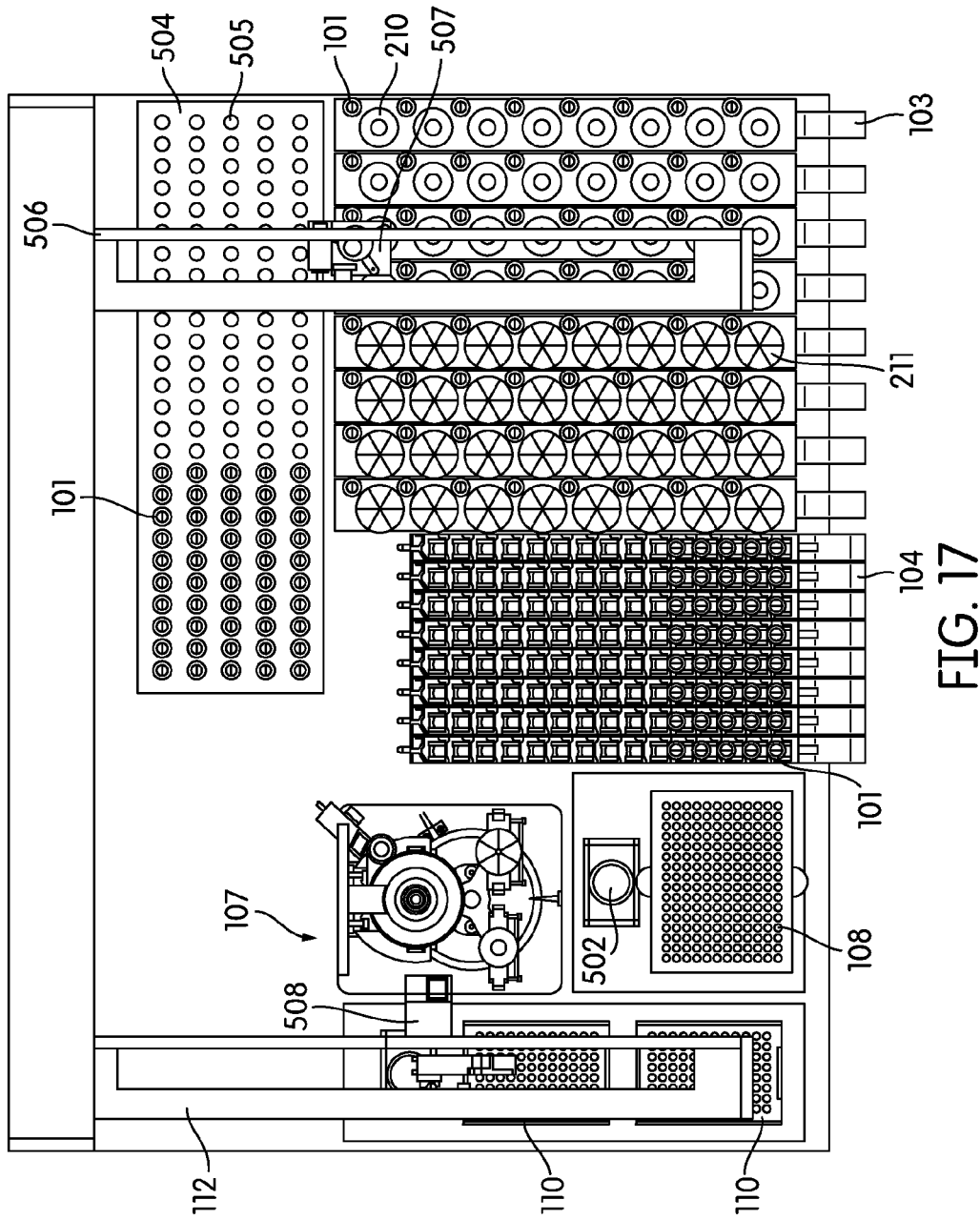
FIG. 17 is a depiction of a top view of the sample handling instrument of FIG. 16.

Although FIGS. 14 and 15 show a single robot arm (112) comprising both the pipettor (406) and the pick and place mechanism (405), multiple robot arms, for example 2 or more, are contemplated for example as depicted in FIGS. 16 and 17. As shown in FIGS. 16 and 17 a second robot arm (506) is provided with a pick and place mechanism (507), while the first robot arm is provided with the pipettor (406). In a related alternative embodiment the first robot arm (112) contains both a pipettor (406) and a pick and place mechanism (405) and the second robot arm (506) contains a pick and place mechanism (507). This second robot arm (506) often serves all pick and place duties required by the instrument. Alternatively, the second robot arm (506) is programmed, by way of the controller to move reaction vessels (101) and sample containers (102, 210, 211) between, for example, the input racks (103) and the sample processing station (107), movement of sample containers (102, 210, 211) from the sample processing station (107) to the input racks (103), movement of reaction vessels (101) from the processing station (107) to the incubator (504) or output racks (104), and/or movement of reaction vessels (101) from the incubator (504) to the output racks (104). Use of multiple robot arms provides multiple advantages, for example by maximizing throughput while permitting uninterrupted processing in the sample processing station (107).

Process Controls

Ensuring sample processing accuracy and completion is an important aspect of any biological sample processing process, whether it is manual or automated. In automated processing, however, it becomes increasingly difficult to determine whether a particular process was carried out, or if it was carried out accurately, since processing often occurs outside the view of the user. Moreover, biological samples such as LBC samples are often complex materials to work with in an automated fashion due to, among other reasons, the frequent occurrence of mucoids, particulates, the risk of contamination between samples, and the presence of specimen collection utensils such as brooms, brushes, spatulas, etc. Mucoids can interfere with sample aspiration and dispense accuracy since they may occasionally hang off the end of a pipette tip after sample aspiration. The increased viscosity of mucoids can also occasionally provide a false indication of the true sample volume that has been aspirated. Moreover, a hanging mucoid at the end of a robot operated pipettor tip poses a significant contamination risk as the pipette winds its way over sample containers, reaction vessels, and/or reagents on its way to a waste bin or other location. Particulates also interfere with sample aspiration and dispense accuracy since they can clog the opening of a pipette tip and give a false indication of the true volume of an aspirated sample, or prevent aspiration altogether.

The present system therefore advantageously provides a variety of process controls with each sample processing protocol to minimize the chance that an incorrectly processed sample is delivered to the user. For example, at each step in the process, encoders, electro-mechanical flags, liquid level detection, barcode reading, temperature sensors, machine vision, optical sensors, reverse cLLD, and pressure base volume verification, as described herein, are used to ensure that specimen and sample tubes, as well as reagents and the specimens themselves, have successfully completed each step in the processing protocol.

If a sample processing protocol fails and the sample cannot be recovered, there are a variety of contemplated options for dealing with such a failure. In one embodiment, if a sample processing fails, the reaction vessel is drained by the pipettor and placed in the output rack. When the sample is later processed on the sample assay instrument, the empty reaction vessel generates a liquid level or dispensing failure. Since the reaction vessel contains the same patient identifying information as its corresponding sample collection container, e.g., barcode information, the sample processing failure can be automatically reported to the laboratory information system (LIS). Alternatively, if a sample processing fails, the reaction vessel is placed in the output rack, but rotated in a manner that the barcode of the vessel cannot be read. Either the user will observe the lack of barcode, or when the sample is processed on the sample assay instrument, the sample assay instrument will determine that particular slot of the output rack (104) to be empty since it will be unable to read identifying information about the reaction vessel in that slot. This empty indication cues the user to report a processing failure to the LIS since the user will identify that a reaction vessel is actually present and that reaction vessel is associated with a particular sample collection container. A third option for dealing with sample processing failure is returning the reaction vessel to the input rack, which optionally leaves an empty slot in the output rack (104). Similar to option two, the user then identifies the reaction vessel (101) in the input rack (103), and/or the user or assay instrument identifies the lack of reaction vessel (101) in the output rack and reports the sample processing failure to the LIS. As another option, the printer on the sample handling instrument can black-out a barcode present in the tube of a failed sample to ensure that the sample cannot be accidentally processed on a down-stream instrument.

Ensuring sample identification accuracy is another problem encountered when automating a sample handling process. For example, as the sample is prepared it is transferred between the sample collection container (102, 210, 211) and the reaction vessel (101). Therefore, it is important to ensure that the sample in the reaction vessel (101) is correlated with the sample in the sample container (102, 210, 211) so that the sample is processed according to the proper protocol and that the correlation of that sample with the donor patient is maintained. To address these issues the instrument advantageously tracks the identification of each sample throughout processing, including following the sample as it is passed from the sample container (102, 210, 211) to the reaction vessel (101). One exemplary method of tracking this information provided herein is to utilize matching barcodes on both the sample container (102, 210, 211) and the reaction vessel (101). This process maintains sample-to-result positive identification tracking. Utilizing this tracking process provides an advantage over existing sample processing instruments in that matching the tube barcodes and always passing the reaction vessel (101) directly to the sample assay instrument eliminates the need for an LIS interface. Moreover, this process greatly simplifies the necessary instrument software and tracking process since the downstream assay instrument is generally connected to an LIS.

The laboratory workflow required to process LBC samples requires that both the LBC sample container (102, 210, 211) and the reaction vessel (101) have the same barcode containing patient identification. This enables sample assay instruments such as instruments capable of performing hybridization assays, amplification assays, sequencing assays, and/or immunoassays to communicate with the laboratory's LIS. Some laboratories do not have the capability, or their process flow does not allow them to, print duplicate barcodes. The present invention addresses these problems in a few alternative ways. For example, if the laboratory has the capability, it can print a barcode containing patient identification and apply it to the sample container (102, 210, 211). The reaction vessel (101), in turn, contains a preprinted, unique serial number on the tube provided by, for example, the tube manufacturer. The sample handling instrument then reads both the sample container (102, 210, 211) barcode and the reaction vessel (101) barcode and creates an association between the two containers. This association information is then transferred to the sample assay instrument via a network connection (e.g., LAN, Ethernet, WiFi, BLUETOOTH®, ZIGBEE®, RS232, USB, RF, IR, FIREWIRE®, THUNDERBOLT®, eSATA, or other). When the sample assay instrument encounters a reaction vessel with patient identification that has the association, the instrument then queries/reports patient data against the associated sample container (102, 210, 211) barcode, which is loaded into the LIS.

Alternatively, the same scenario as above may occur, with the exception that the association information is stored in a file on a mobile storage device such as a USB drive or similar. The mobile storage device is then, for example, manually plugged into the assay instrument where the information is transferred to the instrument. Alternatively, the association information is occasionally stored in an RFID tag positioned, for example, on the output rack. In such an embodiment the RFID tag transmits the information to the assay instrument upon placement in the instrument.

Figure 18:
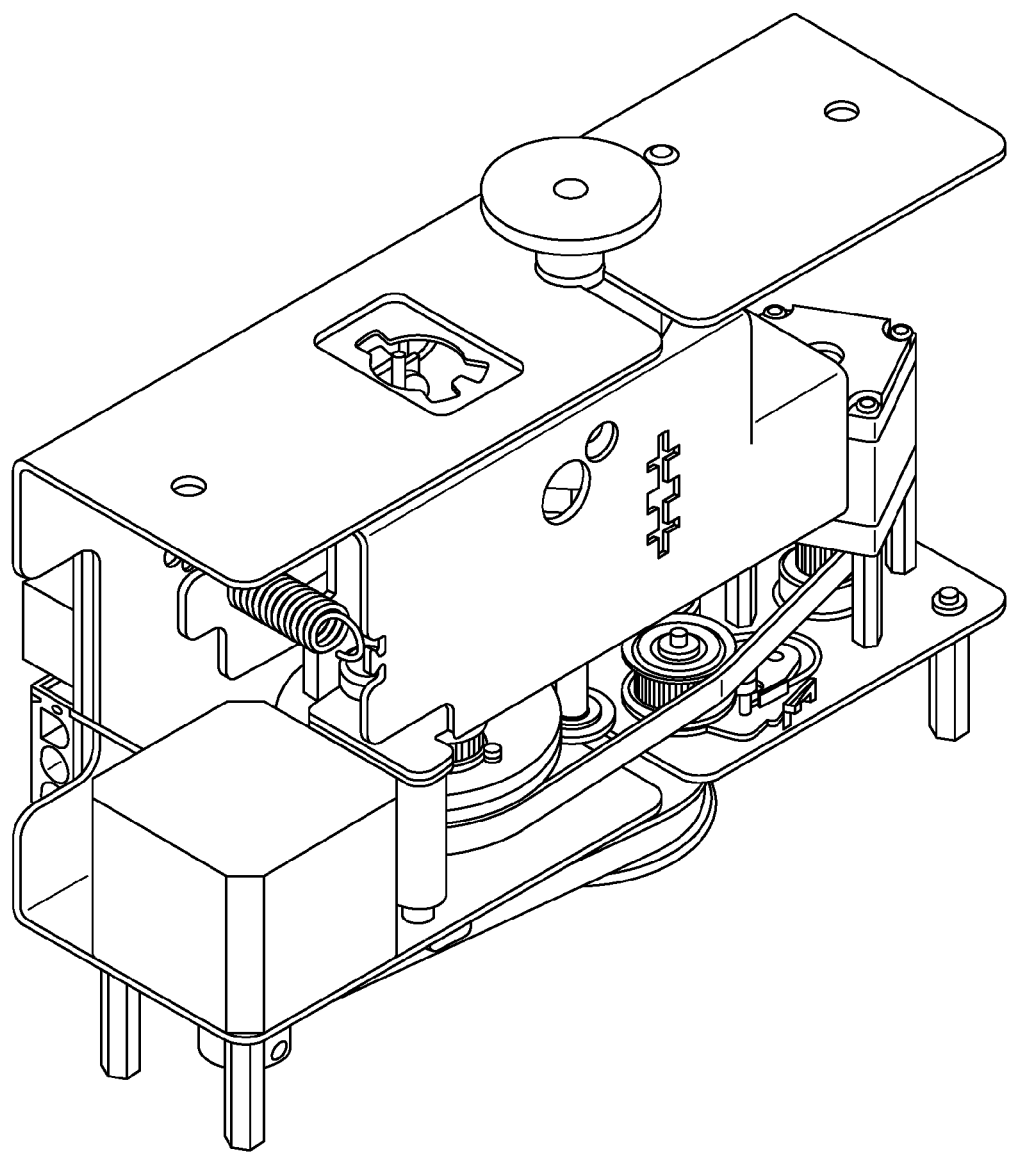
FIG. 18 is a depiction of one embodiment of the printer module.
Figure 19:
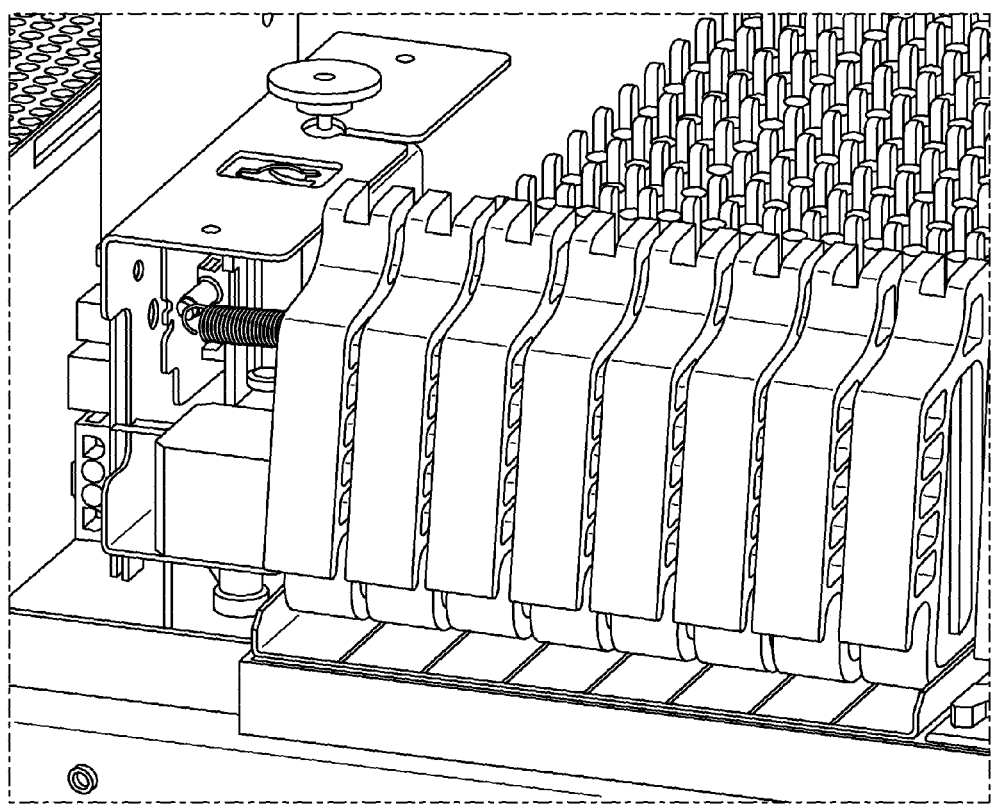
FIG. 19 is a depiction of one exemplary placement of the printer module in the sample handling instrument adjacent to an output rack.

Alternatively, the laboratory prints one barcode containing patient identification and applies it to the sample container (102, 210, 211). The reaction vessel, in turn, contains no label, a blank label, or a different label. The sample handling instrument then reads the sample container (102, 210, 211) barcode, prints the same barcode as contained on the sample container (102, 210, 211) (with optional additional metadata in the form of barcode prefixes, suffixes or similar) and applies it to the reaction vessel (101). In a related preferred embodiment, the sample processing instrument reads the sample container (102, 210, 211) barcode, and creates the same barcode (with optional additional metadata in the form of barcode prefixes, suffixes or similar) directly on the reaction vessel, e.g., by way of printing, imprint, burning, thermal transfer, or another method. Also frequently a different bar code is printed on the reaction vessel containing additional metadata (e.g., time, volume, type, reagents, errors, etc.) related to the processing of the corresponding sample. The barcodes are created in the instrument most frequently through the use of a printer module (FIGS. 18 & 19 pictured) positioned within the instrument. In practice, a sample container is moved from an input rack to the sample processing station to be processed; meanwhile, the corresponding reaction vessel is transferred from the input rack to the printer module. The reaction vessel most frequently has a blank label, or a blank area on the label, where the barcode is to be printed or applied by the printer module. In practice, the printer module automatically determines the orientation of the tube to identify the position to print the barcode. Often the orientation determination is performed with reference to edges of the label or other indicia contained on the label. The means for barcode printing includes any known printing method, for example inkjet, direct thermal, thermal transfer, impact, laser ablation, laser pigment change, etc. It is frequently preferred to utilize thermal transfer printing in the printer module to eliminate the need for extra consumables, contamination risks, among other reasons. After the barcode is printed, or otherwise automatically applied, on the reaction vessel it is transferred to the sample processing station for processing.

In another alternative embodiment, the sample container (102, 210, 211) contains duplicate barcodes, or more than one barcode, and the sample processing instrument removes one of these barcodes and applies it directly on the reaction vessel. The automated assay instrument can then directly query the LIS or report to the LIS against the sample container (102, 210, 211) barcode (i.e., patient ID).

In one embodiment, samples are processed one-at-time in the automated sample handling instrument. For example, when incubation is not required, the next sample does not start its processing until the preceding sample processing is complete. In such an embodiment, the robotic arm pick-and-place mechanism retrieves the sample container (102, 210, 211) and the reaction vessel (101) from the input rack (103). Both containers are moved to the sample processing station (107) where, for example, the barcodes are read (215) by a barcode reader (204) and verified to be a pair. In a preferred embodiment the processing of the sample container begins in the sample processing station prior to arrival of the reaction vessel. In such an embodiment, the reaction vessel is frequently presented to a printer module (FIGS. 18 & 19) by the pick and place mechanism to print a barcode on the reaction vessel prior to its arrival in the sample processing station. The barcode printed, or otherwise applied, on the reaction vessel may be identical to the corresponding sample container or it may be a different bar code. Often a different bar code is incorporated that encodes additional metadata relevant to the processing of that particular sample.

Once processing has been completed, the reaction vessel (101) is moved to the output rack (104) and the sample container (102, 210, 211) is moved back to the input rack (103). All process controls, system status, and user status are logged and associated with the sample barcodes and saved to persistent storage. At any time, the sample processing log can be queried for a specific sample by, for example, barcode, RFID, or exported to a file via, for example, a USB drive or similar.

Figure 12:
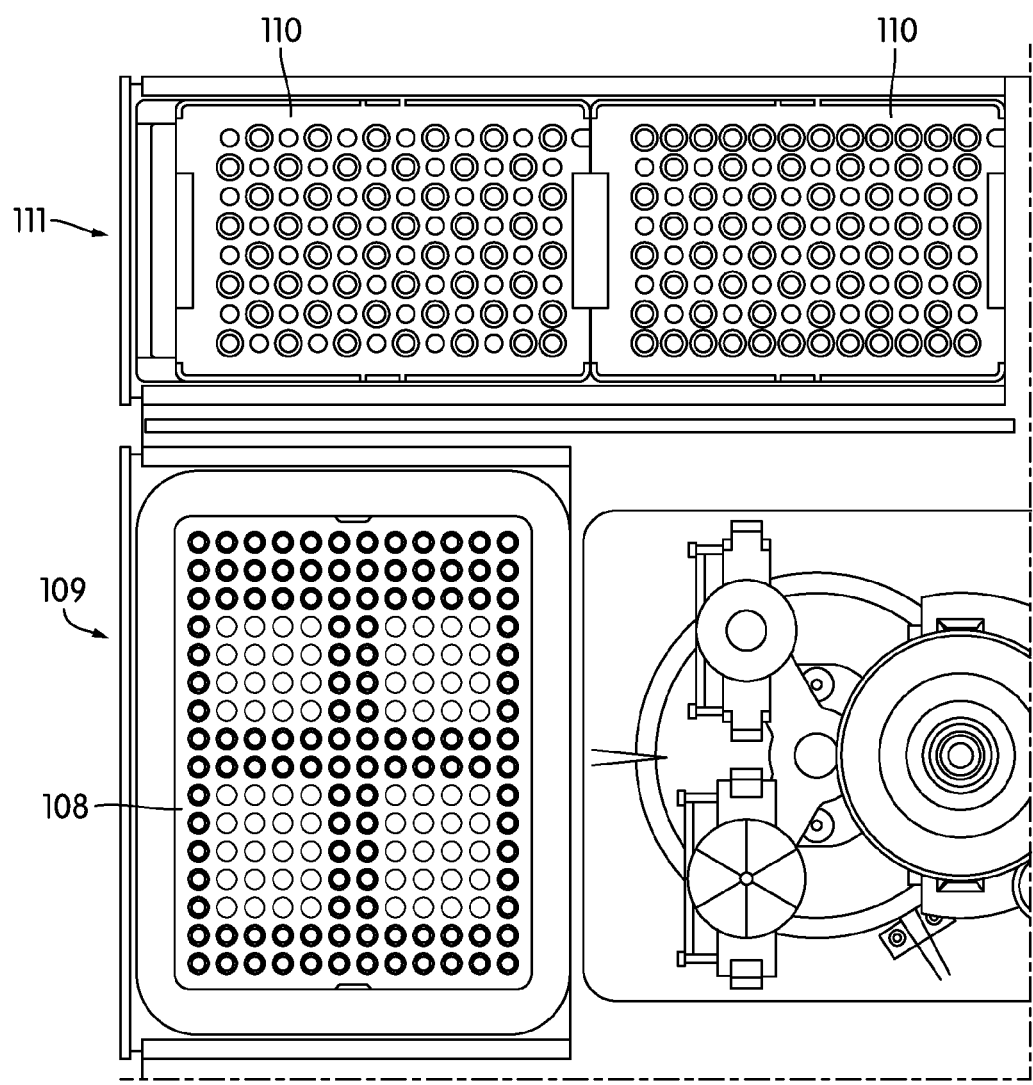
FIG. 12 provides a top view of one embodiment of a consumable inventory management system component.

In most diagnostic instrumentation, inventory control and monitoring is handled by a set of assumptions, rules and feedback mechanisms which are complicated, marginally accurate and time consuming. The automated sample processing instrument of the present invention implements a new concept for fast, accurate, real-time control and monitoring of onboard inventory via machine vision. In practice, each of the inventoried items are visibly available to a set of camera(s) that perform image processing algorithms to determine volume, capacity, or inventory of any onboard consumables, samples, tubes, and waste materials. For example, in one embodiment, one or more cameras are statically mounted on the instrument frame to provide continuous real-time feedback. In addition or alternatively, as shown in FIGS. 16 and 17, one or more cameras (508) are mounted on a robotic arm (112, 506) to provide visual feedback to multiple areas of the instrument. Though FIGS. 16 and 17 depict a single camera (508) on robot arm (112), another camera can be positioned on the second robot arm (506). Special illumination techniques are provided to achieve robust, fast and accurate visual feedback. For example, a few specific areas of machine vision inventory control that are often used on the sample processing instrument are as follows:

1. Pipette Tip & Waste Bin Inventory: A camera is mounted above the instrument looking onto the deck (e.g., FIG. 17). The camera is in optical communication with, and images the pipette tip trays and waste bin. The camera has, for example, onboard image processing capabilities, or is connected to computer or computing apparatus to conduct image processing, and processes the image and provides a full inventory of all tips within the tip trays and waste bin. In one embodiment, backlight illumination under the tips trays and waste bin is provided to reduce the complexity and increase the reliability and speed of the image processing algorithms (see FIG. 12). In one embodiment the tip tray and/or waste bin are made of a translucent material to enhance imaging.

2. LBC Specimen tube Inventory: A camera is mounted above the instrument looking onto the deck (e.g., FIG. 17). The camera is in optical communication with, and images the sample input bay containing the sample container (102, 210, 211) to be processed. The camera, for example, has onboard image processing capabilities, processes the image, and provides a full inventory of all reaction vessels (101) and sample containers (102, 210, 211) present on the instrument. In a related embodiment, the camera is utilized to determine the types of sample containers (102, 210, 211) and/or types of samples contained in the input racks (103), for example by identifying markings on the sample container (102, 210, 211) or sample rack (103), or visualizing a barcode contained on the sample containers (102, 210, 211) or sample rack (103).

3. Single Camera Inventory Control: Alternatively, one or more cameras (508) is/are mounted to an instrument robotic arm (112, 506). The camera (508) is moved around the instrument deck during routine operation of the robotic arm (112, 506) or upon special instruction, providing a full inventory of all instrument consumables as in cases (1) and (2) above.

As mentioned above, a common problem with specimens collected from patients is the presence of mucoids. Pipette tips often get clogged or pull mucoid strands from the sample or specimen tube. While clogs can usually be detected with pressure based feedback, mucoid strands may not be detectable. If mucoids are not properly removed, contamination may occur. While shearing mechanisms may work, they may not guarantee mucoid removal. Thus, the automated sample processing instrument may include a mucoid strand detection mechanism. In a preferred embodiment, the mucoid strand detection mechanism incorporates a machine vision system to visually inspect all pipette tips immediately after a specimen aspiration and before the pipette tip has been moved away from the specimen tube. The vision system frequently comprises a camera such as camera (509) in FIG. 2) with onboard image processing algorithms that notify the instrument controller as to whether or not a mucoid strand is present.

As a second layer of detection for a mucoid strand detection mechanism, the pipettor (406) is optionally configured to perform a reverse capacitive Liquid Level Detection (cLLD) such as described in U.S. Pat. No. 7,479,391. Reverse cLLD detects a change in capacitance of the pipette tip. When the pipette tip is removed from the specimen liquid, cLLD reports a step change in capacitance. This step change occurs at the liquid level of the specimen (the liquid level is accurately detected before aspiration). If the step change is delayed or there is no step change, a mucoid may be present.

When a mucoid strand is detected by either or both processes, the pipettor fully dispenses the sample back into the sample container (102, 210, 211) and re-attempts the aspiration. The pipettor may optionally alter it's position within the sample tube to a new aspiration location to avoid mucoids. If after multiple retries, mucoid strands are still detected, the specimen tube is optionally vortexed and the aspiration process is repeated. This process has the advantage of providing a significant guard against contamination versus conventional shearing mechanisms since no mucoid strands leave the sample container (102, 210, 211). Furthermore, this method requires little or no maintenance, so routine instrument cleaning requirements are reduced.

In a frequent embodiment, the automated sample processing instrument contains one or more of the following process controls to ensure accurate and complete sample processing:

1. Positive sample identification using a barcode reader to read tubes in the processing station.

2. Consumable inventory control of all consumables, the solid waste bin, the input racks, the output racks, and incubator inventory, which can identify the number and type of preparations remaining (e.g., camera-based).

3. Reagents volumes confirmed and tracked by liquid level sense and/or LLD.

4. Liquid in waste bin volume tracking by LLD or counting dispenses.

5. Detection of pipettor tip retention and ejection.

6. Confirmation of sample delivery by liquid level sense and/or Pressure Dispense Volume Verification via RDV.

7. Confirmation of reagent delivery by liquid level sense and/or Pressure Dispenser Volume Verification via RDV.

8. Mix verification by sensing mechanical motion using sensors and/or encoders.

9. Thermal monitoring of all temperature sensitive modules.

10. Encoder feedback to ensure proper robotic motion.

11. Machine vision mucoid detection.

12. Sensors to detect different sample types (e.g., input racks).

13. Positive ID verification and barcode printing for reaction vessels in the instrument.

In another frequent embodiment, the automated sample handling instrument contains one or more of the following process controls to minimize the risk of contamination:

1. Filtered disposable pipette tips.
2. Cleanable specimen input racks.
3. Cleanable output racks.
4. Cleanable consumable rack.
5. Disposable waste bins or waste bin covers.
6. Cleanable drip tray.
7. Specimen mucoid removal track.
8. Barriers between the tip racks, sample racks, and processing station.
9. Controlled airflow to keep aerosols moving from clean to less clean side of instrument.
10. Easily cleanable surfaces and tracks.
11. Instrument covers to protect from splashing the operator.
12. Machine vision and reverse cLLD confirmation of sample aspiration and mucoid detection.

Since the instrument is capable of concurrently processing multiple sample types, some requiring reagent addition and heated incubation and others not requiring incubation, it is important to ensure proper thermal management. In this regard, in one embodiment the automated sample processing instrument often contains one or more of the following items:

1. Four or more incubators servicing four or more output racks; alternatively a single incubator is provided, servicing all reaction vessels to be incubated.
2. Multiple temperature sensors that provide precision incubator temperature control and redundancy.
3. Controlled airflow.
4. Insulated incubators that inhibit heat transfer to other parts of the instrument containing reaction vessels that are not to be incubated, sample containers, and reagents.

Throughput

The present invention provides an automated high-throughput, random access sample handling instrument capable of simultaneously processing multiple different sample types. As indicated, the instrument automatically processes samples according to a rule set that balances throughput with time-to-next-result, which is particularly relevant when the instrument is processing different types of samples that require different routines and reagents. For example, in one embodiment the instrument is designed to process up to about 540 samples that do not require incubation, or up to about 360 samples that require reagent addition and heated incubation within a single 8 hour shift. Included in this time is instrument setup, run preparation, sample handling, clean up and instrument power down. For purposes of this discussion, a "run" is defined as the processing of up to about 60 LCB specimens from start to finish. One of skill in the art would appreciate that a run could involve processing more or fewer samples, depending on the number of available input and output slots on the machine. For example, a run could refer to the processing of up to about 96 LCB specimens from start to finish. In one embodiment a run refers to processing a collection of samples that occupy a defined portion or all of the available input slots or that occupy a defined portion or all of the available output slots.

The sample processing protocol that does not require incubation (i.e., processing THINPREP® samples) is often the LBC preparation protocol executed on the instrument having the fewest steps. In a frequently preferred embodiment, this protocol takes about 1 minute of processing time per specimen and thus can process up to 9 runs (e.g., 540 samples) in an 8 hour shift. In this embodiment the time to first result is about 1 minute for a single specimen or approximately 15 minutes to prepare a full output rack having 15 slots.

In another embodiment, the protocol takes about 30 seconds of processing time per specimen, and thus can process up to 18 runs (e.g., 1080 samples) in an 8 hour shift. In this embodiment the time to first result is approximately 30 seconds for a single specimen or approximately 7.5 minutes to prepare a full output rack having 15 slots.

The specimen processing time will often depend on the type of processing required and the sample type being prepared. The overall sample processing protocol can vary over a range of time, for example processing of a single sample may range from 30 seconds to 2.5 hours (if incubation is required). In a frequently preferred embodiment the sample processing time may range between 30 seconds and 2 minutes. In another preferred embodiment the sample processing time may range between about 1 to about 2 minutes. If an incubation is required, often sample processing time will range between about 1 hour to about 2.5 hours.

Figure 4:
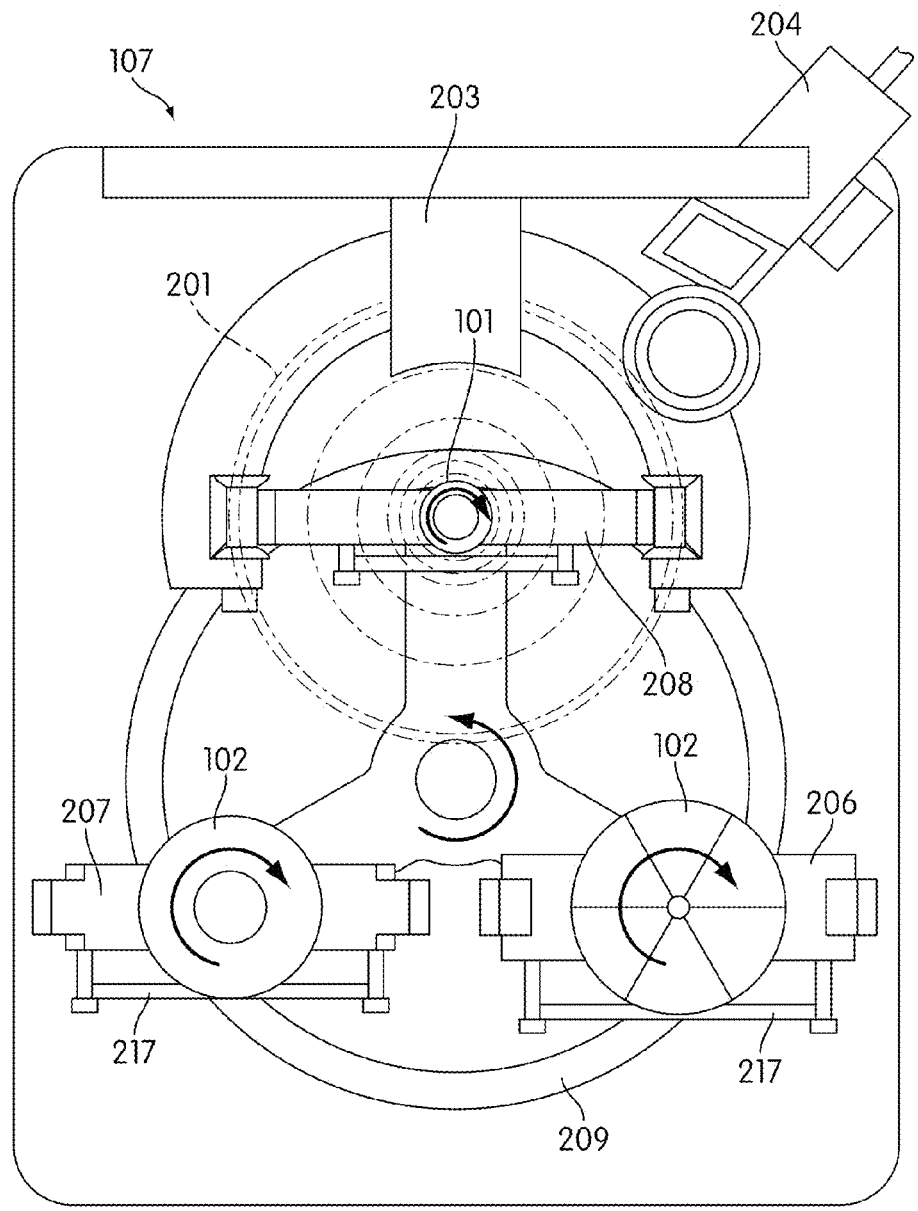
FIG. 4 provides a top view of an exemplary sample processing station, showing exemplary rotational directions of the carousel, sample containers and reaction vessel.
Figure 5:
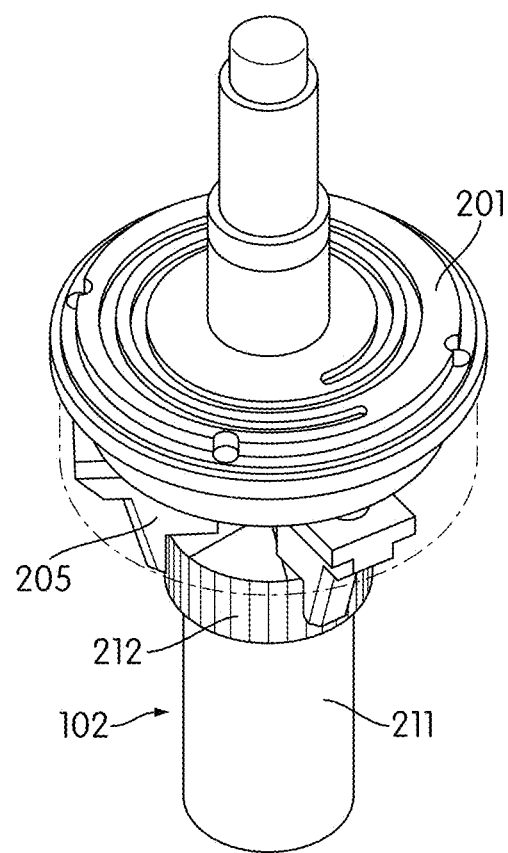
FIG. 5 provides a perspective view of an exemplary capping and decapping mechanism.
Figure 6:
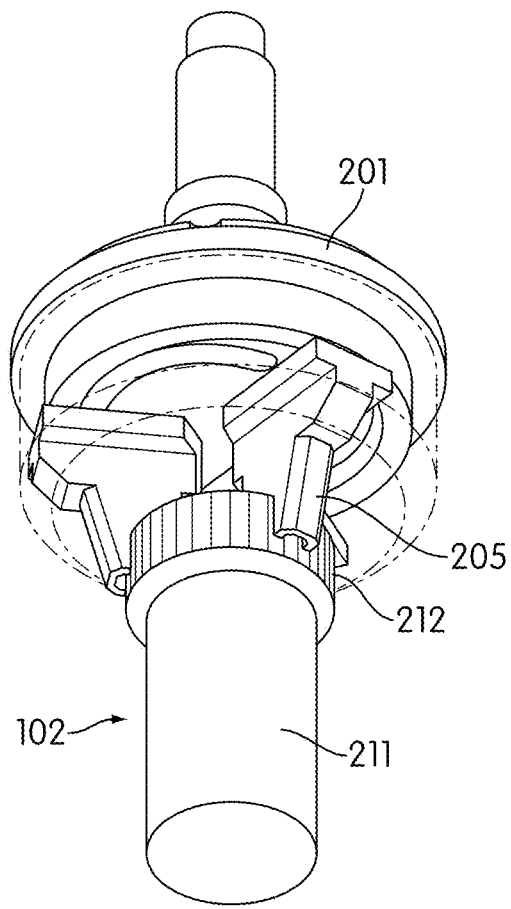
FIG. 6 provides another perspective view of an exemplary capping and decapping mechanism.

In one embodiment, the flow of processing of a THINPREP® sample, irrespective of concurrently conducted process controls, is the following:

a. Pick sample container (211) from input rack and place in corresponding container holsters (206, 208, respectively) on carousel (209) in processing station (107);

b. Read the sample barcode;

c. Orbital mixing (see arrows on FIG. 4);

d. If necessary, pick corresponding reaction vessel (101) from input rack and place in printer module (FIGS. 18 & 19) for barcode printing;

e. Pick corresponding reaction vessel (101) from printer module (FIGS. 18 & 19) and place in reaction vessel holster (208) on carousel (209) in processing station (107);

f. Rotate sample container (211) under elevator (203) holding capping/decapping mechanism (201) where chuck (205) grasps cap (212) (see also FIGS. 5 & 6);

g. Uncap Thinprep container (211);

h. Elevator (203) moves cap/chuck (212/205) upward, which permits the carousel (209) to rotate without hitting the cap, and the drip tray (202) swings under the chuck/cap (212/205);

i. Rotate sample container (211) to service position (i.e., the positioning depicted for container (211) in FIG. 2);

j. Aspirate sample from sample container (211);

k. Move pipettor (406) over liquid waste container (502);

l. Rotate sample container (211) under capping/decapping mechanism (201) and chuck (205);

m. Move drip tray (202) out of way of chuck (212/205);

n. Elevator (203) moves capping/decapping mechanism (201) holding cap/chuck (212/205) downward onto sample container (211) and drip tray (202) is withdrawn;

o. Sample container (211) is recapped;

p. Move elevator (203) up to allow carousel (209) to rotate;

q. Reaction vessel is rotated under capping/decapping mechanism (201);

r. Elevator (203) is lowered where chuck (205) grasps and removes reaction vessel cap (216);

s. Elevator (203) moves cap/chuck (216/205) upward and the drip tray (202) swings below the cap/chuck (216/205);

t. Move drip tray (202) under cap (216/205);

u. Reaction vessel (101) is rotated to the service position;

v. Sample is dispensed into the reaction vessel (101);

w. Reaction vessel (101) is rotated under capping/decapping mechanism (201) and chuck (205);

x. Drip tray (202) is withdrawn as the elevator (203) moves cap/chuck (216/205) downward onto reaction vessel (101) to recap the reaction vessel (101);

y. Reaction vessel (101) is recapped;

z. Sample container (211) is moved to input rack (103);

aa. Reaction vessel is moved to output rack (104).

In one embodiment, the flow of processing of a SUREPATH® sample, irrespective of concurrently conducted process controls, is the following:

a. Pick sample container (210) from input rack and place in corresponding container holsters (207, 208, respectively) on carousel (209) in processing station (107);

b. Read the sample barcode;

c. Mix (see arrows on FIG. 4);

d. If necessary, pick corresponding reaction vessel (101) from input rack and place in printer module (FIGS. 18 & 19) for barcode printing;

e. Pick corresponding reaction vessel (101) from printer module (FIGS. 18 & 19) and place in reaction vessel holster (208) on carousel (209) in processing station (107);

f. Rotate sample container (210) under elevator (203) holding capping/decapping mechanism (201) where chuck (205) grasps cap (213) (see also FIGS. 5 & 6);

g. Uncap sample container (210);

h. Elevator (203) moves cap/chuck (213/205) upward, which permits the carousel (209) to rotate without hitting cap(213), and the drip tray (202) swings under the chuck/cap (213/205);

i. Rotate sample container (210) to service position (i.e., the positioning depicted for container (211) in FIG. 2);

j. Pipettor (406) aspirates predetermined amount of sample processing reagent (e.g., FASTEXPRESS® reagent, available from Gen-Probe Incorporated, San Diego, Calif.);

k. Using the same pipette tip as step (g), or selecting a new pipette tip, aspirate sample from sample container (210);

l. Move pipettor (406) over liquid waste container (502);

m. Rotate sample container (210) under capping/decapping mechanism (201) and chuck (205);

n. Elevator (203) moves capping/decapping mechanism (201) holding cap/chuck (213/205) downward onto sample container (210) and drip tray (202) is withdrawn;

o. Sample container (210) is recapped;

p. Move elevator (203) up to allow carousel (209) to rotate;

q. Reaction vessel (101) is rotated under capping/decapping mechanism (201);

r. Elevator (203) is lowered where chuck (205) grasps and removes reaction vessel cap (216);

s. Elevator (203) moves cap/chuck (216/205) upward and the drip tray (202) swings below the cap/chuck (216/205);

t. Reaction vessel (101) is rotated to the service position;

u. Sample is dispensed into the reaction vessel (101);

v. Reaction vessel is rotated under capping/decapping mechanism (201) and chuck (205);

w. Drip tray (202) is withdrawn as the elevator (203) moves cap/chuck (216/205) downward onto reaction vessel (101) to recap the vessel;

x. Reaction vessel (101) is recapped;

y. Sample container (210) is moved to input rack (103);

z. Reaction vessel (101) is optionally mixed;

aa. Reaction vessel (101) is moved to output rack/incubator (104/105) or dedicated incubator (504) for incubation;

bb. If reaction vessel (101) is positioned in dedicated incubator (504), after incubation the reaction vessel (101) is moved to output rack (104).

One of skill in the art that one or more of the above processes can occur simultaneously. The above automated protocols are provided by way of example only such that modifications of the number of steps, what happens in each step, and the number of processes occurring in a particular order or simultaneously may be changed or altered without affecting the subject matter of the present invention.

One of skill in the art would appreciate that the processing time required to process each sample has a direct effect on the number of samples that can be prepared in a given time period. Manipulation of the processing time may have a detrimental impact on processing accuracy and can increase the risk of contamination, though a variety of sample processing times are contemplated with the caveat that downtime between sample processing is kept to a minimum.

Sample processing protocols that incorporate a reagent addition and/or incubation step (e.g., processing SUREPATH® samples) are slightly more complicated than non-reagent or non-incubation protocols. In the case of processing SUREPATH® samples a reagent addition step and an incubation step are required to fully prepare a sample. The rate limiting step for SUREPATH® samples in a frequent embodiment is the incubation time for samples requiring incubation. For example, a 2 hour sample incubation at 65° C. will affect the overall throughput of the instrument. Instrument downtime can be minimized and throughput can be maximized in batches of samples containing samples requiring incubation by reducing incubation times (e.g., down to about 1 hour), increasing the number of samples incubated at any given time, and/or reducing the number of slots in the output rack.

Sample incubation time can vary over a period of time. For example, in the case of an LBC sample the incubation time can be about 15 minutes, about 30 minutes, about 45 minutes, about 60 minutes, about 75 minutes, about 90 minutes, about 105 minutes, or about 120 minutes. The incubation temperature occasionally varies as well. For example, the incubation temperature may be at or about 37° C., at or about 65° C., or between about 37° C. and 65° C. Occasionally, the incubation time may be at or about 90° C., or between about 37° C. and 90° C. In occasional embodiments the incubation temperature is above or below 65° C. In an occasional embodiment requiring incubation in output racks, the instrument will generally fully populate an output rack with, e.g., 15 samples before the incubation process is started. In such an embodiment the processing time is about 1 minute 30 seconds, or about a minute, or about less than a minute per sample prior to the incubation step.

In the frequently preferred embodiment that provides incubation of reaction vessels in a dedicated incubator (rather than in the sample output rack) having about 120 incubation slots, high throughput rates can be maintained since incubation may begin when a reaction vessel is positioned in the incubator, without having to wait until an output rack is fully populated. The sample processing instrument, for example, can be configured to monitor the incubation time of each reaction vessel contained in the dedicated incubator. Similarly, in such an embodiment a large number of samples can be incubated at any particular time without commandeering output rack space, thus permitting a continuous flow of non-incubated samples through to the input racks while concurrently processing samples requiring incubation. Although the processing time for any particular batch (e.g., a full output rack of, for example, 15 samples) of incubated samples occasionally does not decrease though the use of a dedicated incubator, throughput advantages are realized since output rack use flexibility is maximized. For example, any particular output rack can be populated with samples containing reaction vessels that have been incubated and those that have not been incubated. In such an embodiment involving an output rack having, for example, 15 slots, these slots can be filled with up to 15 reaction vessels that have been incubated and up to 15 reaction vessels that have not been incubated. In such circumstances it is unnecessary to await the completion of the incubation of 15 reaction vessels to fill an output rack; rather the rack can be populated with any number of reaction vessels that have completed their incubation, while the remaining slots in the output rack are filled with non-incubated reaction vessels. Accordingly, in a frequently preferred embodiment the sample processing instrument is capable of processing one sample per minute during the entirety of an 8 hour work day, excluding instrument startup and shutdown time, regardless of whether the samples require incubation or not.

It will be understood by one of skill in the art that varying incubation time, the number of slots in a sample output rack, and/or permitting partial filling an output rack will correspondingly affect the time to completion of one or more samples, including a batch of samples. For example, if the incubation time is reduced from 2 hours, the number of incubation slots can be decreased while maintaining a similar throughput. Unless specifically indicated, the present invention is not limited to a specific incubation time, amount of samples in a sample input rack, number of sample input rack slots, number of slots in an output rack, number of output rack slots, number of incubators, number of robotic arms, number of pick-and-place mechanisms, or number of sample processing stations.

In one embodiment the instrument is modular such that the number of incubator slots can be altered to more or fewer than 120. In addition, the sample processing instrument may be outfitted with additional sample input or output slots, for example 4, 5, 6, 7, 8 or more input or output slots, which permits increased walk-away time by the user while increasing system throughput.

In one embodiment the instrument is designed to process any combination of sample racks containing samples requiring and not requiring incubation at anytime, while minimizing dead time. This feature allows the user random access to the instrument in batches of 1-8 specimens (an exemplary number of specimen held in an input rack). The instrument software will balance time to next result and throughput based on a defined set of rules, taking into account the incubation time required for the samples in the system. In a preferred embodiment, the sample processing rules are the following: (1) Finish loading current output rack, (2) process all samples requiring incubation up to incubation, and (3) process all samples not requiring incubation. Often in such an embodiment the output rack may be populated with incubated and non-incubated samples, depending on how many samples completed their incubations while the output rack was being populated. For example, in one embodiment when a sample completes incubation it is immediately transferred to the next available slot in an output rack, whether it is an empty or partially filled output rack. One of skill in the art would understand that the time period between incubation completion and transfer to an output rack may be limited by, for example, the availability of the pick and place mechanism of the instrument to effect such a transfer.

As noted, the instrument is designed to maximize throughput regardless of the type of sample being processed. The embodiments and examples discussed herein are provided by way of illustration only. As noted, the number of input and output slots (including number of incubators) can be decreased or increased in a manner that will affect overall throughput, with the limiting factors comprising incubation time and processing time within the sample processing station. Accordingly, in one embodiment the instrument incorporates one or more sample processing station(s) together with, optionally, a correspondingly increased number of input slots and incubator slots and robot arms containing a pipettor and/or pick and place mechanisms. It is contemplated that this configuration will increase the throughput versus the examples discussed above, but at the expense of a larger bench-top footprint.

Another limiting factor to increasing throughput is the overall footprint of the instrument. Often laboratory space is very limited such that only smaller, bench-top style instruments can be accommodated. The present invention fulfills this need by providing a fully automated sample processing solution in a compact package. As such, it is an object of the present invention to provide a compact instrument capable of automated sample processing of multiple sample types. For example, in one preferred embodiment the instrument is a bench-top instrument.

Capacity

The consumable and liquid/solid waste capacity often dictate the maximum number of tests the instrument can perform before specimen processing is stopped and consumables are reloaded and waste is removed. In one embodiment the consumables and waste bins are sized for processing a maximum of 96 samples. In another embodiment, the consumables and waste bins are sized for processing a maximum of 192 samples. In a further embodiment, the consumables and waste bins are sized to accommodate the number of samples and volume of liquid and solid waste generated in a full shift of use of the instrument, such as processing up to about 540 samples.

The waste bin is frequently used in the event that a sample processing fails, where the failed sample is discarded in the waste bin. In addition, in one embodiment the waste bin is utilized as part of the sample processing process where it acts as a drip catch for caps removed from sample containers (102, 210, 211) and pipette tips containing sample or reagent. In one embodiment, this drip catch can be utilized during the period of time it takes the sample processing station carousel (209) to rotate to the service position (depicted in FIG. 2) for sample aspiration or dispense. In another embodiment, a drip catch or drip tray (202) is included as a component of the sample processing station (107). In an occasional embodiment, the drip catch or drip tray comprises a portion that is in fluid communication with the liquid waste bin and another portion capable of positioning below (a) a cap removed from a sample container, or (b) a pipette tip containing sample or reagent. In any event, the liquid waste bin (502) is frequently configured to have a capacity to hold all the liquid waste generated in a single shift or a single day of operation.

In one embodiment, the input racks (103) are sized to hold up to about 8 LBC sample containers (102, 210, 211) in addition to 8 reaction vessels (101). In this embodiment the instrument is designed to hold up to 8 input racks (103) for a total of 64 LBC samples. To run 540 samples that do not require additional reagents or incubation, the 8 sample input racks (103) are loaded 9 times, for example. In the case where samples requiring additional reagent and incubation are processed, the input racks (103) are loaded 6 times to process 360 LBC specimens, for example.

In one exemplary embodiment the output drawer is sized to contain at least 4 or up to about 8 output racks (104), each capable of holding 15 reaction vessels for a total of 120 reaction vessels. The instrument can be configured to require that the output racks (104) have their top covers (304), if otherwise part of the output rack, removed while being used in the instrument, which permits loading of the reaction vessels (101) into the racks. In this example, to process 540 samples, involves removal of 36 output racks (104), and to process 360 samples involves removal of 24 output racks (104) over the course of a shift.

In one embodiment, the instrument has one or more drawers or cabinets dedicated to consumables and waste. Pipette tip trays (110) (e.g., two or more trays of 96 pipette tips) are loaded into the consumable drawer or cabinet along with one or more reagent bottle(s) (503) required for samples requiring additional reagent. Frequently, a barcode reader (not pictured) is incorporated in optical communication with the consumable drawer or cabinet, such that when the drawer is closed or consumables are placed in the cabinet, one or more of the consumables are then scanned to determine various information about the consumable, for example, lot number, expiration date, total volume, volume remaining, type of reagent, etc. Often, however, the consumables are scanned prior to closing the cabinet or drawer. In such embodiments the particular consumable, for example the reagent bottle, will contain a barcode encoding the necessary or desired information.

In one embodiment, the reagent bottle (503) will generally have sufficient volume to process at least 96 samples, or at least about 120 samples, or at least about 190 samples, or up to about 360 samples, requiring additional reagent (e.g., SUREPATH® samples). Additional reagent bottles, or a larger reagent bottle, may alternatively be incorporated. For example, in one embodiment the reagent bottle (503) will generally have sufficient volume to process at least all of the samples in a shift, or multiple shifts. The consumable drawer or cabinet is often locked so the user cannot inadvertently open it during operation.

Preparing and Loading the Instrument

In one exemplary embodiment, the first step in preparing the instrument for a run is to service the consumable drawer. In one embodiment, the instrument will display the number of remaining samples that it can process before requiring replenishment of reagents, pipette tips, emptying of waste bins, shifting reaction vessels to an output rack, replacement of input racks, and/or replacement of output racks. If the number of remaining samples to be processed is less than the desired number of preparations to be performed, the consumable drawer will often be accessed and loaded/emptied. The instrument is then capable of tracking what pipette tips have been used and how many tips are left, for example, by use of machine vision. See FIG. 12, for example. The reagent bottle (503) is, in one embodiment, monitored by a liquid level sensor to determine the number of remaining preparations that can be performed with the remaining reagent. In a preferred embodiment, the liquid level detection functionality of the pipettor is utilized to monitor the amount of reagent remaining in the reagent bottle (503). With regard to solid waste, the waste bin (108) can be emptied each time the waste bin drawer is opened The next step in this embodiment is to apply matching barcode labels to the sample containers (102, 210, 211) and the reaction vessels (101) and load them into the appropriate sample input rack. Once all input racks (103) have been loaded, they are inserted into the instrument. In an exemplary embodiment machine vision is utilized to detect the container or vessel positions in each rack that are populated to provide a full inventory of input racks (103) in the instrument.

In another step of this embodiment, the output racks (104) are loaded into the instrument. The output racks (104) have their top cover (304) removed (if present) and also must be empty. In an exemplary embodiment machine vision is utilized to check or verify whether the output racks (104) are empty. If a newly inserted output rack (104) is not empty the system will notify the user.

In another step of this embodiment machine vision is utilized to track the inventory of the incubator (504). Machine vision, therefore, as it is utilized in the present instrument can accurately determine, at any given time, the inventory of the instrument, including the incubator (504), input racks(103), output racks (104), solid waste bin (108), and tip trays (110).

Instrument Fluidic Management

In a preferred embodiment the instrument incorporates a variety of measures and devices to ensure controlled fluid management. For example, in one embodiment the instrument has a single pipettor arm (112) with a pipettor (406) that utilizes both capacitive and pressure based fluid detection (LLD) and pressure based aspiration/dispense verification (RDV). In this embodiment a precision dry syringe pump is used to accurately aspirate and dispense volumes from, for example, 25 to 1000 μL. The syringe pump will often include a rotary encoder to verify the motor has not stalled or failed. Built into the pump between the syringe and the pipette tip is a pressure transducer that records the pressure waveform when dispensing and/or aspiration occurs. Characteristics of the curve are used to verify dispense/aspiration process (RDV). A conductive pipette tip is frequently attached to the syringe pump through a stainless steel interface that conducts an oscillating current, used to measure changes in capacitance. When the pipette tip touches fluid, the capacitance changes and can be detected through the liquid level detection (LLD) circuitry. See, e.g., U.S. Pat. Nos. 4,977,786, 5,083,470, and 7,479,391, each of which is incorporated herein by reference.

The fluid levels in the reagent bottles are often detected with LLD, and the volume is calculated based on the known bottle geometry. The reagent bottle is frequently keyed in such a way that it cannot be mixed up with other bottles within the system.

In a frequent embodiment, waste fluid is removed from failed reaction vessels and placed in the liquid waste reservoir using the pipettor. In this circumstance, the targeted reaction vessels will be liquid level detected to determine the amount of liquid to be removed. Liquid waste will be aspirated from the reaction vessel and dispensed into the liquid waste bin. The level of the liquid waste reservoir is also measured by LLD to notify the user when servicing is required.

Electronics Design

Figure 13:
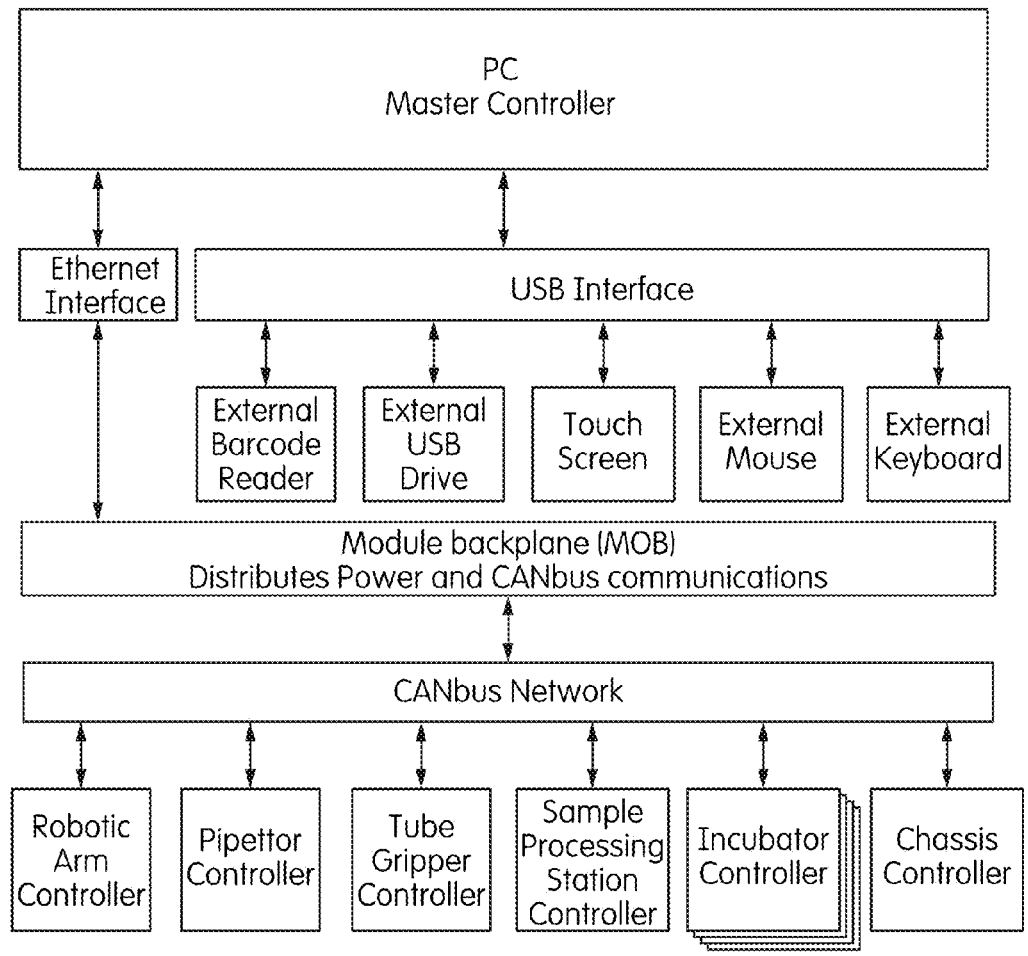
FIG. 13 provides a chart depicting one embodiment of an exemplary electronic controller architecture of the present disclosure.

In one embodiment, the electronic design for the instrument includes a Controller Area Network (CANbus) that distributes power and communications between the master PC controller and the system modules. The CANbus and all System peripherals are interfaced to the master PC controller via Ethernet and USB interfaces, for example as depicted in FIG. 13.

In another preferred embodiment, the electronic design for the instrument relies on power line communication (PLC), which permits communication signals to be transmitted over power lines in the instrument. See, e.g., POWER LINE COMMUNICATIONS: THEORY AND APPLICATIONS FOR NARROWBAND AND BROADBAND COMMUNICATIONS OVER POWER LINES (H. C. Ferreira et al. eds., John Wiley & Sons Ltd. 2010). PLC offers certain advantages over CANbus, such as permitting high data transfer rates and utilization of a variety of protocols, such as the CANbus protocol, TCP/IP, among others. Moreover, PLC reduces complexity in the system while offering increased reliability by reducing the number of wires/cables extending between instrument parts. PLC is especially advantageous in moving parts since the number of potential wire/cable pinch-points are reduced and less area is occupied by wires/cables and, if present, their associated conduits.

In one frequent embodiment, the PC will run a stripped down OS. Any time critical activities are handled at the module controller level, and each module has its own controller responsible for running its specific tasks. Commands are, for example, sent down to the modules via the CANbus network. Each module controller contains its own specific set of commands and parameters. Controllers are able to post module status to the master controller at anytime.

All documents referred to herein are hereby incorporated by reference herein. No document, however, is admitted to be prior art to the claimed subject matter.

While the invention has been described in connection with what are presently considered to be the most practical and preferred embodiments, it is to be understood that the invention is not to be limited to the disclosed embodiments, but, on the contrary, is intended to cover various modifications and equivalent arrangements included within the spirit and scope of the appended claims.

Furthermore, those of the appended claims which do not include language in the "means for performing a specified function" format permitted under 35 U.S.C. §¶6, are not intended to be interpreted under 35 U.S.C. §¶6, as being limited to the structure, material, or acts described in the present specification and their equivalents.

The invention claimed is:

1. A processing station for automatically processing a biological sample, comprising:
   (a) a rotatable platform configured to rotate around a central axis;
   (b) two or more container holders arranged in spatially distinct locations on the rotatable platform, wherein each of the container holders is configured to hold a container and wherein the rotatable platform is configured to mix a fluid sample contained within the container;
   (c) a capping/decapping mechanism configured to decap and cap a container positioned in one of the two or more container holders;
   (d) an automated pipettor comprising a pipette tip configured to selectively aspirate an amount of fluid into the pipette tip or dispense an amount of fluid from the pipette tip and to move the pipette tip with respect to the rotatable platform to enable the pipette tip to access a container carried on the rotatable platform; and
   (e) mucoid strand detection means for detecting the presence of a mucoid strand suspended from the pipette tip, wherein the rotatable platform, the capping/decapping mechanism, the automated pipettor, and the mucoid strand detection means are in operative communication with a controller programmed to:
      (i) activate the rotatable platform to move a container positioned in one of the two or more container holders into a capping/decapping position,
      (ii) activate the capping/decapping mechanism to remove a cap from the container,
      (iv) activate the rotatable platform to move the container to a fluid transfer position,
      (v) activate the automated pipettor to move the pipette tip into the fluid sample within the container, aspirate an amount of the fluid sample into the pipette tip, and withdraw the pipette tip from the fluid sample,
      (vi) after the automated pipettor has aspirated the amount of the fluid sample from the container and withdrawn the pipette tip from the fluid sample within the container but before the automated pipettor moves the pipette tip away from the container, determine if there is a mucoid strand on the pipette tip with the mucoid strand detection means, and
      (vii) if a mucoid strand is detected, activate the automated pipettor to dispense the aspirated fluid sample back into the container.

2. The processing station of claim 1, further comprising a drip tray operatively located with respect to the capping/decapping mechanism and controlled by the controller and configured to be movable between a first position not under the capping/decapping mechanism and a second position under the capping/decapping mechanism.

3. The processing station of claim 1, wherein the mucoid strand detection means comprises a machine vision system and a reverse capacitive liquid level detection system.

4. The processing station of claim 1, wherein two or more container holders are positioned on the periphery of the rotatable platform.

5. The processing station of claim 1, wherein each container holder is adapted to rotate around an individual secondary axis of rotation that is different than the secondary axis of each other container holder.

6. The processing station of claim 1, wherein the rotatable platform is configured to orbitally mix the contents of each container.

7. The processing station of claim 6, wherein the rotatable platform is configured to rotate circularly around the central axis together the two or more container holders circularly around their secondary axes in a direction opposite of the rotation of the rotatable platform.

8. The processing station of claim 1, further comprising a data scanning mechanism configured to scan information on an outer surface of a container while the container is positioned in one of the two or more container holders.

9. The processing station of claim 1, wherein the station comprises three container holders.

10. The processing station of claim 2, wherein the drip tray is configured to translate in a radial plane relative to the central axis.

11. The processing station of claim 10, wherein the motion of the drip tray, when translated comprises rotation about a tertiary axis that is different than the central axis of the rotatable platform.

12. The processing station of claim 11, wherein the drip tray extends outwardly from the tertiary axis.

13. The processing station of claim 12, wherein the extension is effected by way of an arm, post, plate, panel, or blade extending outwardly from the tertiary axis.

14. The processing station of claim 1, wherein each of the container holders is configured to hold different containers, the different containers comprise two or more different containers, and at least one of the two or more different containers has a width, height, and/or diameter that differs from one other of the two or more different containers.

15. The processing station of claim 8, wherein the data scanning mechanism comprises a barcode scanner.

16. The processing station of claim 15, wherein the barcode scanner is utilized to determine the centerline and/or position of a barcode on a sample container or reaction vessel.

17. The processing station of claim 1, further comprising an incubator adapted to heat at least a portion of the contents of the container.

18. The processing station of claim 1, wherein elements (b)-(g) are comprised in a housing.

19. The processing station of claim 17, wherein elements (b)-(g) and the incubator are comprised in a housing.

20. The processing station of claim 18, further comprising a pick and place mechanism controlled by the controller and configured to move each of the two or more containers to different locations within the housing.

21. The processing station of claim 20, further comprising an incubator situated within the housing controlled by the controller and configured to heat at least a portion of the contents of the container.

22. The processing station of claim 18, further comprising a printer module in data communication with the data scanning mechanism, wherein the printer module is comprised in the housing.

23. The processing station of claim 22, wherein the printer module is controlled by the controller and configured to print a bar code containing information about the container, the container's contents, or an assay to be performed utilizing the container's contents.

24. The processing station of claim 1, further comprising a printer module controlled by the controller and configured to apply machine-readable indicia on a surface of a reaction vessel, the machine-readable indicia applied to the reaction vessel including indicia relating to information scanned on the container by the data scanning mechanism, and
wherein the automated pipettor is controlled by the controller and configured to move from the container at the fluid transfer position to the reaction vessel and dispense at least a portion of the aspirated sample material into the reaction vessel.

25. The processing station of claim 24, wherein the information scanned on the container and the machine readable indicia applied to the reaction vessel comprise bar codes.

26. The processing station of claim 25, wherein the bar code on the container and the bar code applied to the reaction vessel are at least partially identical.

27. The processing station of claim 24, wherein the printer is a thermal printer configured to print indicia onto a label on the reaction vessel comprising thermally sensitive print media.

28. The processing station of claim 24, wherein the information scanned on the container by the data scanning mechanism comprises sample-identifying information, and wherein the machine-readable indicia applied onto the surface of the reaction vessel by the printer module is at least partially identical to the information scanned on the container by the data scanning mechanism.

29. The processing station of claim 28, wherein the machine-readable indicia applied on the surface of the reaction vessel includes additional machine-readable indicia that is different from the information scanned on the container by the data scanning mechanism, wherein information relating to one or more of time, volume, type, reagents, and errors is encoded in the additional machine-readable indicia.

30. The processing station of claim 3, wherein the mucoid strand detection means consists of the machine vision system.

31. The processing station of claim 3, wherein the mucoid strand detection means consists of the reverse capacitive liquid level detection system.

32. The processing station of claim 8, wherein the information scanned by the data scanning mechanism comprises information about the container or its contents that is transmitted from the data scanning mechanism to a user interface, a laboratory information system, and/or a PC controller using a power line.

* * * * *